(12) United States Patent
Cronenberg et al.

(10) Patent No.: US 10,391,245 B2
(45) Date of Patent: Aug. 27, 2019

(54) MEDICAMENT DEVICE

(71) Applicant: Becton, Dickinson and Company, Franklin Lakes, NJ (US)

(72) Inventors: Richard Cronenberg, Mahwah, NJ (US); Abhijitsinh Raj, Morris Plains, NJ (US); Matthieu Charvin, Grenoble (FR); David Booth, West Milford, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 523 days.

(21) Appl. No.: 15/100,251

(22) PCT Filed: Dec. 1, 2014

(86) PCT No.: PCT/US2014/067925
§ 371 (c)(1),
(2) Date: May 27, 2016

(87) PCT Pub. No.: WO2015/081337
PCT Pub. Date: Jun. 4, 2015

(65) Prior Publication Data
US 2017/0028132 A1  Feb. 2, 2017

Related U.S. Application Data

(60) Provisional application No. 61/910,373, filed on Dec. 1, 2013.

(51) Int. Cl.
*A61M 5/20* (2006.01)
*A61M 5/24* (2006.01)
(Continued)

(52) U.S. Cl.
CPC .............. *A61M 5/20* (2013.01); *A61M 5/142* (2013.01); *A61M 5/1454* (2013.01);
(Continued)

(58) Field of Classification Search
CPC ...... A61M 5/20; A61M 5/142; A61M 5/1454; A61M 5/162; A61M 5/2455;
(Continued)

(56) References Cited

U.S. PATENT DOCUMENTS 2,911,123 A * 11/1959 Saccomanno ......... A61M 5/162
215/247
4,543,101 A * 9/1985 Crouch ................. A61J 1/2096
604/411

(Continued)

FOREIGN PATENT DOCUMENTS

CN 102971027 A 3/2013
CN 204446979 U 7/2015
(Continued)

*Primary Examiner* — Lauren P Farrar
(74) *Attorney, Agent, or Firm* — Dickinson Wright PLLC

(57) ABSTRACT

A method for creating a sterile connection with a fluid in a container. The container has a sealing member sealing a first end of the container, and a barrier sealing a chamber in fluid communication with the sealing member. The method includes providing a valve sleeve assembly that includes a flexible sleeve having a barrier portion at an end of the flexible sleeve, a hollow first penetrator disposed within the flexible sleeve, and a hollow second penetrator at least partially disposed within the first penetrator. An interior of the flexible sleeve is sterile. The method also includes piercing the barrier portion and the barrier with the first penetrator, and displacing the second penetrator relative to the first penetrator and the sealing member to pierce the sealing member and establish the sterile connection with an interior of the container.

23 Claims, 29 Drawing Sheets

(51) Int. Cl.
  *A61M 5/142* (2006.01)
  *A61M 5/145* (2006.01)
  *A61M 5/162* (2006.01)
  *A61M 5/315* (2006.01)
(52) U.S. Cl.
  CPC .......... *A61M 5/162* (2013.01); *A61M 5/2455* (2013.01); *A61M 5/2459* (2013.01); *A61M 5/2466* (2013.01); *A61M 5/31568* (2013.01); *A61M 2005/206* (2013.01); *A61M 2005/247* (2013.01); *A61M 2005/2414* (2013.01)
(58) Field of Classification Search
  CPC .............. A61M 5/2459; A61M 5/2466; A61M 5/31568; A61M 2005/206; A61M 2005/2414; A61M 2005/247
  See application file for complete search history.

(56) References Cited

U.S. PATENT DOCUMENTS

| | | |
|---|---|---|
| 4,564,054 A | 1/1986 | Gustavsson |
| 4,673,404 A | 6/1987 | Gustavsson |
| 4,785,859 A | 11/1988 | Gustavsson et al. |
| 4,932,937 A | 6/1990 | Gustavsson et al. |
| 5,279,570 A | 1/1994 | Dombrowski et al. |
| 5,360,410 A | 11/1994 | Wacks |
| 6,409,708 B1 | 6/2002 | Wessman |
| 6,602,239 B2 | 8/2003 | Ronneklev |
| 6,715,520 B2 | 4/2004 | Andreasson et al. |
| 7,306,584 B2 | 12/2007 | Wessman et al. |
| 7,743,799 B2 | 6/2010 | Mosler et al. |
| 7,744,581 B2 | 6/2010 | Wallen et al. |
| 7,942,860 B2 | 5/2011 | Horppu |
| 2002/0115981 A1 | 8/2002 | Wessman |
| 2003/0144633 A1 | 7/2003 | Kirchhofer |
| 2003/0187420 A1 | 10/2003 | Akerlund et al. |
| 2005/0182383 A1 | 8/2005 | Wallen |
| 2005/0215976 A1 | 9/2005 | Wallen |
| 2008/0223484 A1 | 9/2008 | Horppu |
| 2008/0277021 A1 | 11/2008 | Horppu et al. |
| 2008/0312633 A1 | 12/2008 | Ellstrom |
| 2008/0312634 A1 | 12/2008 | Helmerson et al. |
| 2009/0057258 A1 | 3/2009 | Tornqvist |
| 2009/0069783 A1 | 3/2009 | Ellstrom et al. |
| 2010/0004602 A1 | 1/2010 | Nord et al. |
| 2010/0022953 A1 | 1/2010 | Bochenko et al. |
| 2010/0147402 A1 | 6/2010 | Tornqvist |
| 2010/0152669 A1 | 6/2010 | Rosenquist |
| 2010/0249745 A1 | 9/2010 | Ellstrom |
| 2011/0125128 A1 | 5/2011 | Nord et al. |
| 2012/0056019 A1 | 3/2012 | Renz et al. |
| 2012/0211946 A1 | 8/2012 | Halili et al. |
| 2012/0215183 A1 | 8/2012 | Halili et al. |
| 2013/0110049 A1 | 5/2013 | Cronenberg et al. |
| 2013/0226081 A1 | 8/2013 | Davies et al. |

FOREIGN PATENT DOCUMENTS

| | | | |
|---|---|---|---|
| FR | 2717086 | 9/1995 | |
| FR | 2717086 A1 * | 9/1995 | ............ A61J 1/2096 |
| WO | WO-2005112573 | 12/2005 | |
| WO | WO-2010/127691 A1 | 11/2010 | |

* cited by examiner

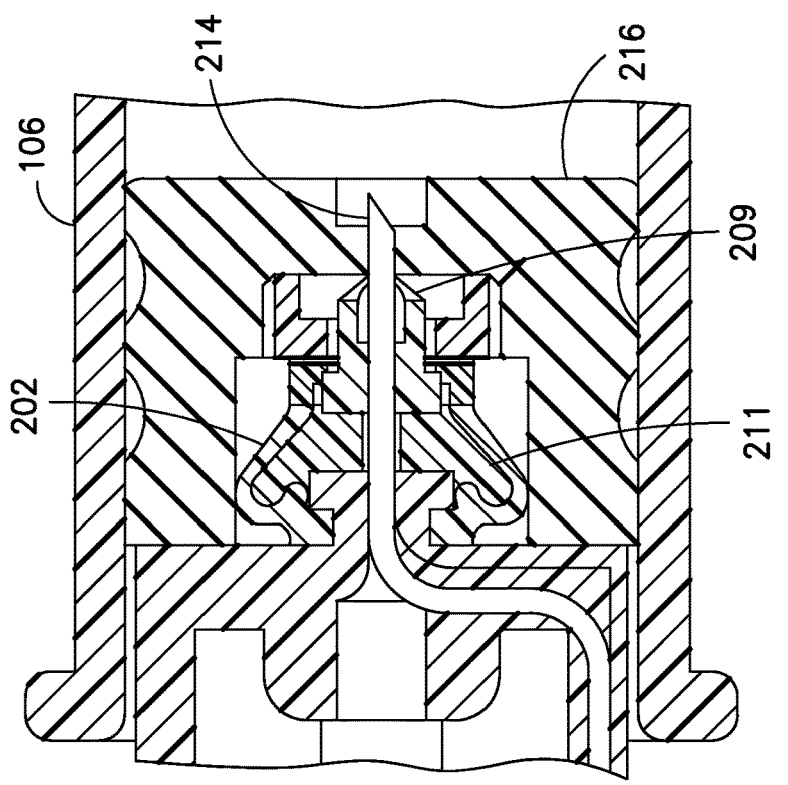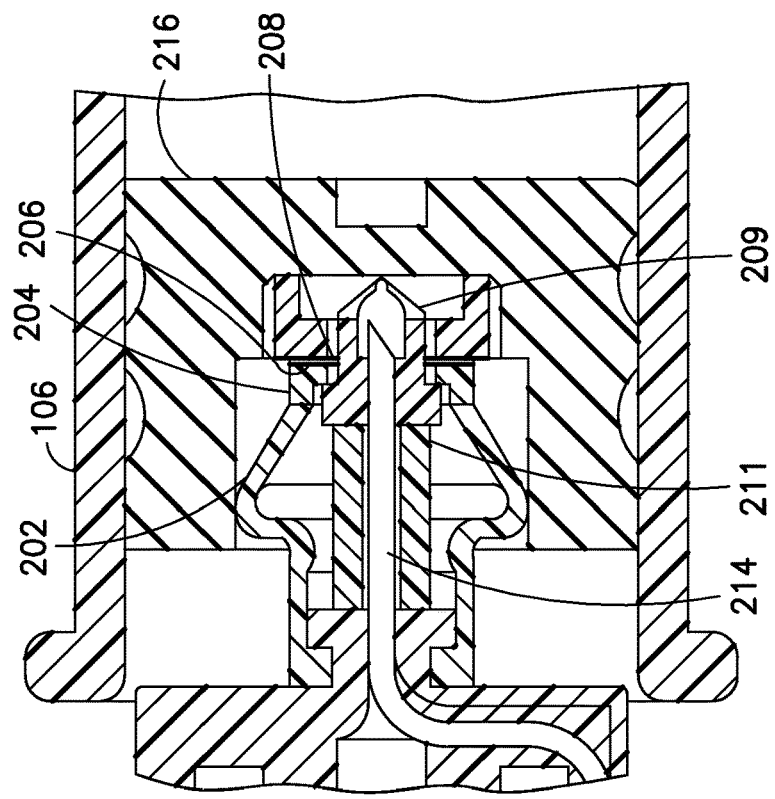
FIG.12

MEDICAMENT DEVICE

CROSS-REFERENCE TO RELATED APPLICATIONS

This application claims priority under 35 USC § 119(e) from U.S. Provisional Patent Application Ser. No. 61/910,373, filed on Dec. 1, 2013, the disclosure of which is incorporated herein by reference in its entirety.

BACKGROUND OF THE INVENTION

1. Field of the Invention

The present invention relates to methods and devices for making a sterile connection, and more particularly, to methods and devices for making a sterile connection with a medicament source.

2. Description of the Related Art

Drug delivery devices in the form of infusers are known in the prior art for administering medicament to a patient. Infusers are intended for mounting onto a patient's skin for self-administration of a medicament. Activation of the infuser not only provides for injection of a needle into a patient's skin, but also to cause auto-drive of a plunger to drive medicament into the patient via the injected needle. Typical infuser constructions have the needle fixed to the reservoir. For example, U.S. Pat. No. 5,858,001 to Tsals et al., discloses an infuser that is activated through swivel displacement of a reservoir-containing body. A needle is fixed to the body to move therewith so that the swivel displacement of the body also causes the needle to penetrate the patient's skin. Other types of infusers are known, including those which use standard needle-mounted syringe barrels. With many infusers, the ability to control the insertion of the needle independent of the administration of medicament is limited.

U.S. Pat. No. 5,290,254 to Vaillancourt discloses a shielded cannula assembly that includes a tubular shield mounted over a cannula. The shield includes a resilient collapsible portion that collapses in an accordion-like manner when a longitudinal force is imposed on the shield.

U.S. Pat. No. 5,685,866 to Lopez discloses a needleless valve with a generally tubular body defining an internal cavity. The valve includes a hollow spike with a closed tip and a hole located in the tip. The spike is seated inside the cavity so that the tip is below the proximal end of the body. An annular support cuff is connected to the spike and seals off a portion of the cavity to define an upper portion of the cavity that includes the tip. The valve also includes a plastic, resilient silicone seal that fills the upper portion of cavity and the body opening, and covers the tip of the spike to present a flush surface.

U.S. Patent Publication No. 2010/00022953 discloses a conduit assembly connected to a medication receiving conduit. The conduit assembly includes a cartridge receiving conduit surrounded by a sleeve, and a conduit sterility cap. A cartridge includes a spring-loaded casing, a cartridge sterility cap, and mechanical features for connecting with the conduit assembly. Upon such connection, an end of the cartridge breaches the conduit sterility cap. Subsequently, the spring drives the casing toward the cartridge receiving conduit, impales the cartridge sterility cap on the sleeve, and connects an interior of the casing with the cartridge receiving conduit.

PCT Publication WO 2011/146166, which is hereby incorporated by reference in its entirety, discloses an infuser in which activation of an actuator causes a spring to move a stopper in a reservoir from a first position toward a second position, and also causes a needle driver to displace a patient needle from a first state toward a second state. The needle moves relative to the reservoir, and separately from the stopper.

In addition, with medical devices, such as syringes and infusion devices, making a sterile connection with a medicament storage device, such as a medicament vial, generally necessitates maintaining the sterility of all parts of the connection, or making the parts of the connection sterile immediately prior to making the connection. Improvements in the equipment and/or the process of making a sterile connection with a medicament storage device are desirable.

SUMMARY OF EMBODIMENTS OF THE INVENTION

Accordingly, it is an aspect of the present invention to provide an improved apparatus and method for making a sterile connection.

The foregoing and/or other aspects of the present invention are achieved by providing an apparatus for making a sterile connection, including a container, a sealing member sealing a first end of the container, a barrier sealing a chamber in fluid communication with the sealing member, and a valve sleeve assembly. The valve assembly includes a flexible sleeve having a barrier portion at an end of the flexible sleeve, a hollow first penetrator adapted to displace relative to the flexible sleeve, and a hollow second penetrator at least partially disposed within the first penetrator and adapted to displace relative to the first penetrator and the flexible sleeve. An interior of the flexible sleeve is sterile. In an initial state, the flexible sleeve encloses the first penetrator and a penetrating end of the second penetrator. One of the container and the valve sleeve assembly is adapted to displace relative to the remaining one of the container and the valve sleeve assembly. The flexible sleeve is adapted to collapse, thereby displacing the outer penetrator relative to the flexible sleeve to pierce the barrier portion and the barrier. Upon further relative displacement between the container and the valve sleeve assembly, subsequent to the piercing of the barrier portion and the barrier, the second penetrator is adapted displace relative to the first penetrator, through the chamber, to pierce the sealing member to create a sterile connection with the interior of the container.

The foregoing and other aspects of the present invention are also achieved by providing a method for creating a sterile connection with a fluid in a container. The container has a sealing member sealing a first end of the container, and a barrier sealing a chamber in fluid communication with the sealing member. The method includes providing a valve sleeve assembly that includes a flexible sleeve having a barrier portion at an end of the flexible sleeve, a hollow first penetrator disposed within the flexible sleeve, and a hollow second penetrator at least partially disposed within the first penetrator. An interior of the flexible sleeve is sterile. The method also includes piercing the barrier portion and the barrier with the first penetrator, and displacing the second penetrator relative to the first penetrator and the sealing member to pierce the sealing member and establish the sterile connection with an interior of the container Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description in conjunction with the accompanying drawings, in which:

FIG. 12 is a cross-sectional view of operation of the mechanism of FIG. 11;

DETAILED DESCRIPTION OF EMBODIMENTS OF THE PRESENT INVENTION

Figure 1:
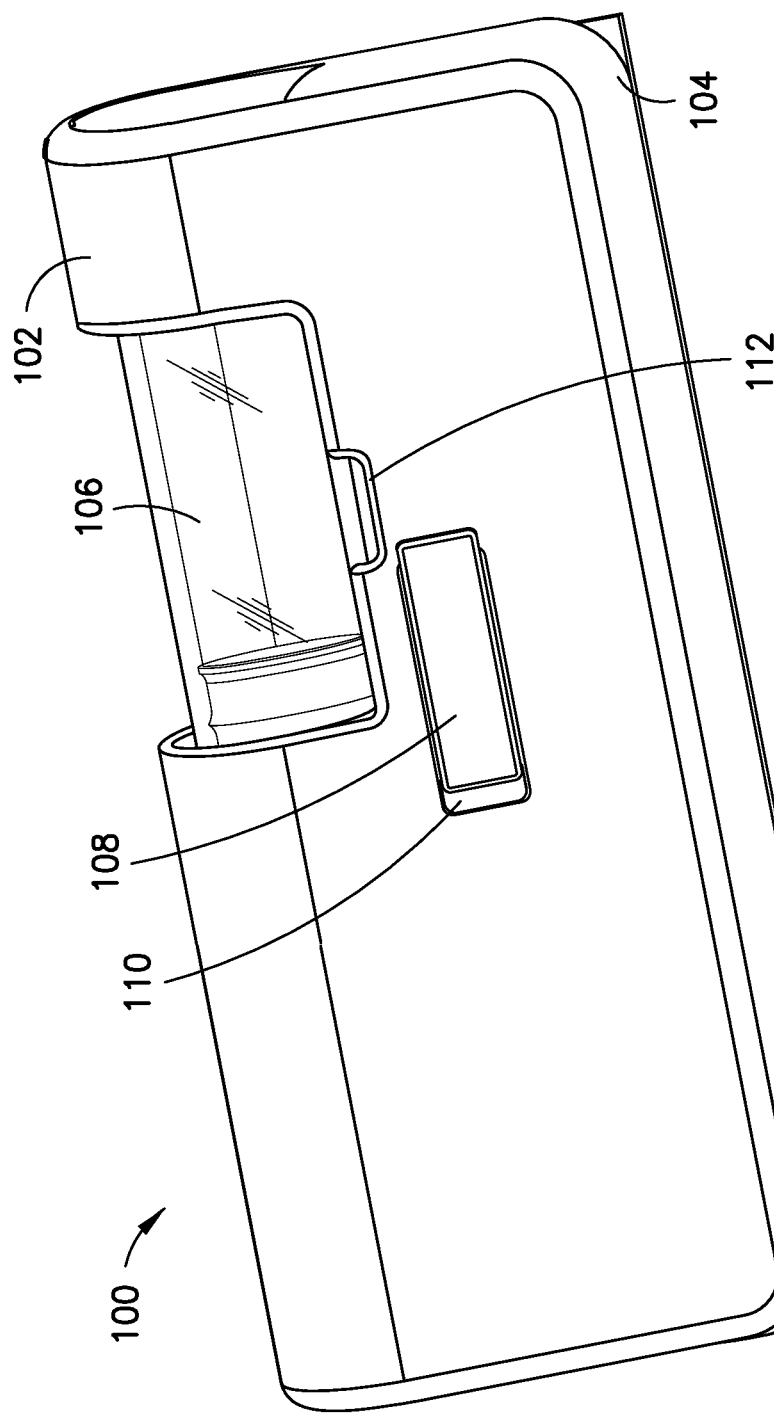
FIG. 1 is a top perspective view of an infusion device in accordance with an embodiment of the present invention.

Detailed reference will now be made to embodiments of the present invention, which are illustrated in the accompanying drawings, wherein like reference numerals refer to like elements throughout. The described embodiments exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used is for description and should not be regarded as limiting. The use of words such as "including," "comprising," or "having" and variations thereof herein is meant to encompass the items listed thereafter and equivalents thereof as well as additional items. Unless limited otherwise, the terms "connected," "coupled," and "mounted," and variations thereof are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The methods and devices of embodiments of the invention include both bolus injection or "injection" and infusion or "infuser" delivery of drugs and other substances to humans or animals subjects. Using the present invention, pharmaceutical compounds may be administered as a bolus injection, or by infusion. As used herein, the term "bolus injection" is intended to mean an amount that is delivered within a time period of less than ten (10) minutes. "Infusion" is intended to mean the delivery of a substance over a time period greater than ten (10) minutes. It is understood that bolus administration or delivery can be carried out with rate controlling means or have no specific rate controlling means. Such rate controlling means include programmed delivery of substances, for example, in a pulsatile manner, by way of example, substances administered via a bolus followed by a short or long term infusion. A bolus dose is a single dose delivered in a single volume unit over a relatively brief period of time, typically less than about 10 minutes. Infusion administration comprises administering a fluid at a selected rate that may be constant or variable, over a relatively more extended time period, typically greater than about 10 minutes Although the following embodiments are directed to infusion devices, it will be understood by those skilled in the art that embodiments of the present invention are not limited to infusion devices, and instead, can include injectors, or any type of device for making a sterile connection with a storage device (such as a medicament storage device). For brevity, however, the illustrated embodiments are generally referred to as infusion devices.

FIG. 1 is a top perspective view of an infusion device or infuser 100 for infusing a medicament into a patient. Although a user other than a medicament recipient (for example, a health care professional) can use the device 100, for brevity, the term "user" will be employed to refer to a patient and/or other user. The device 100 includes a top cover 102, a bottom cover 104, a medicament barrel 106, a top button portion 108, and a bottom button portion 110. As described in greater detail below, the top cover 102 prevents the top button portion 108 from being depressed until a user slides the button longitudinally (proximally, or to the left in FIG. 1). The device 100 also includes an indicator window 112, through which the user can see a progress indicator 114 to aid in determining the completion of the dose.

Figure 2:
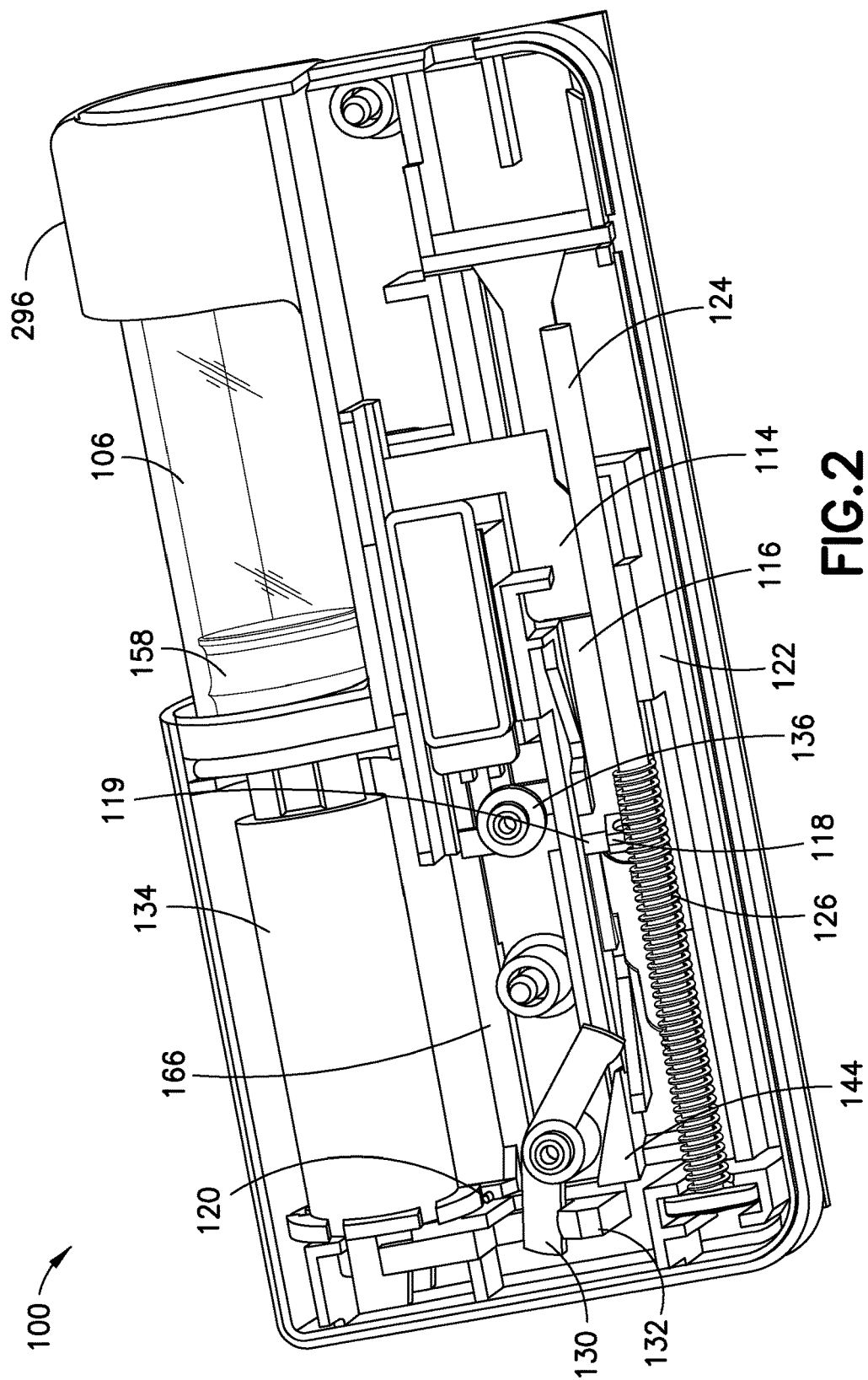
FIG. 2 is a top perspective view of the device of FIG. 1 with a several elements removed for clarity.
Figure 3:
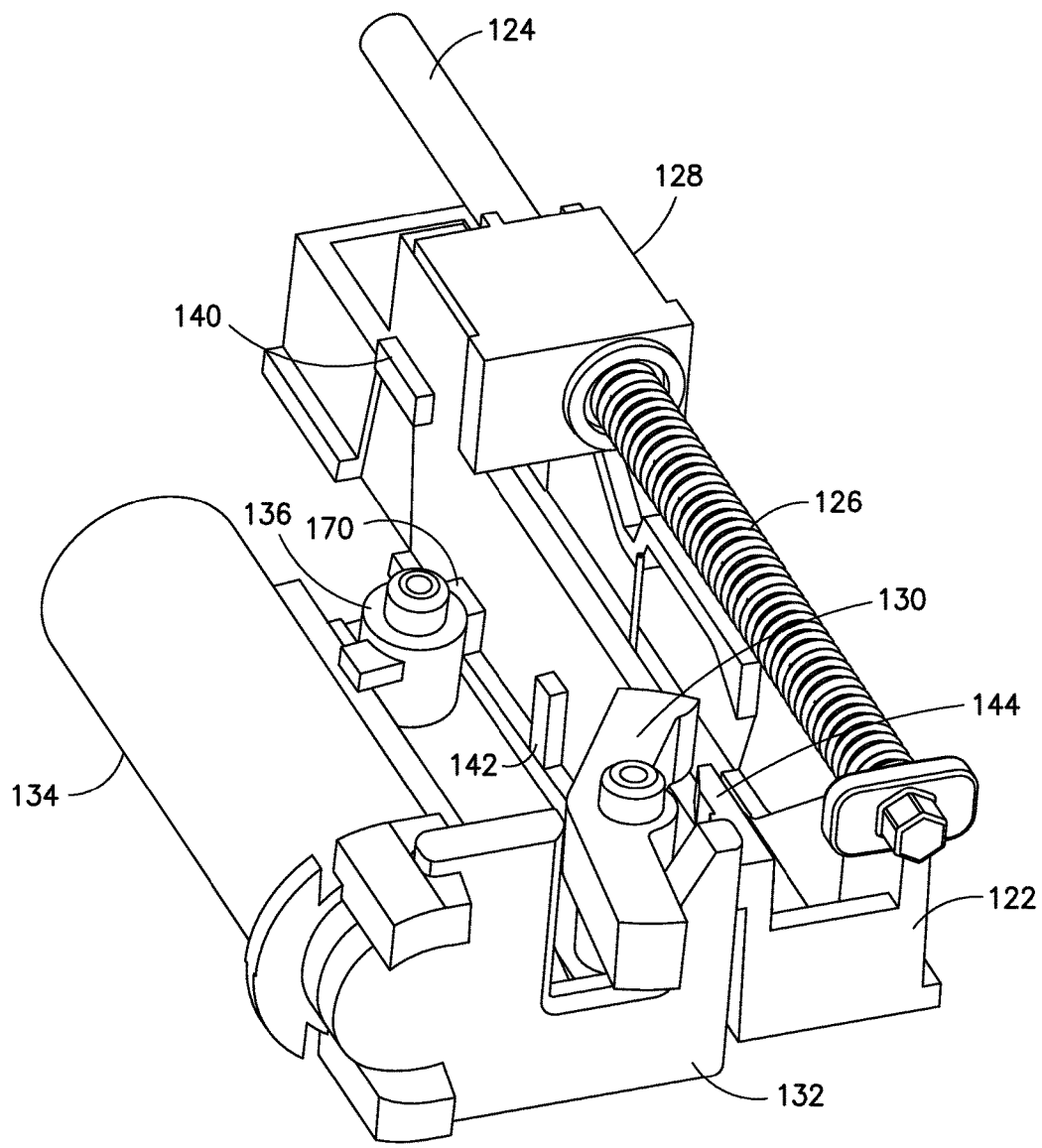
FIG. 3 is a perspective view of elements of the device of FIG. 1.
Figure 4:
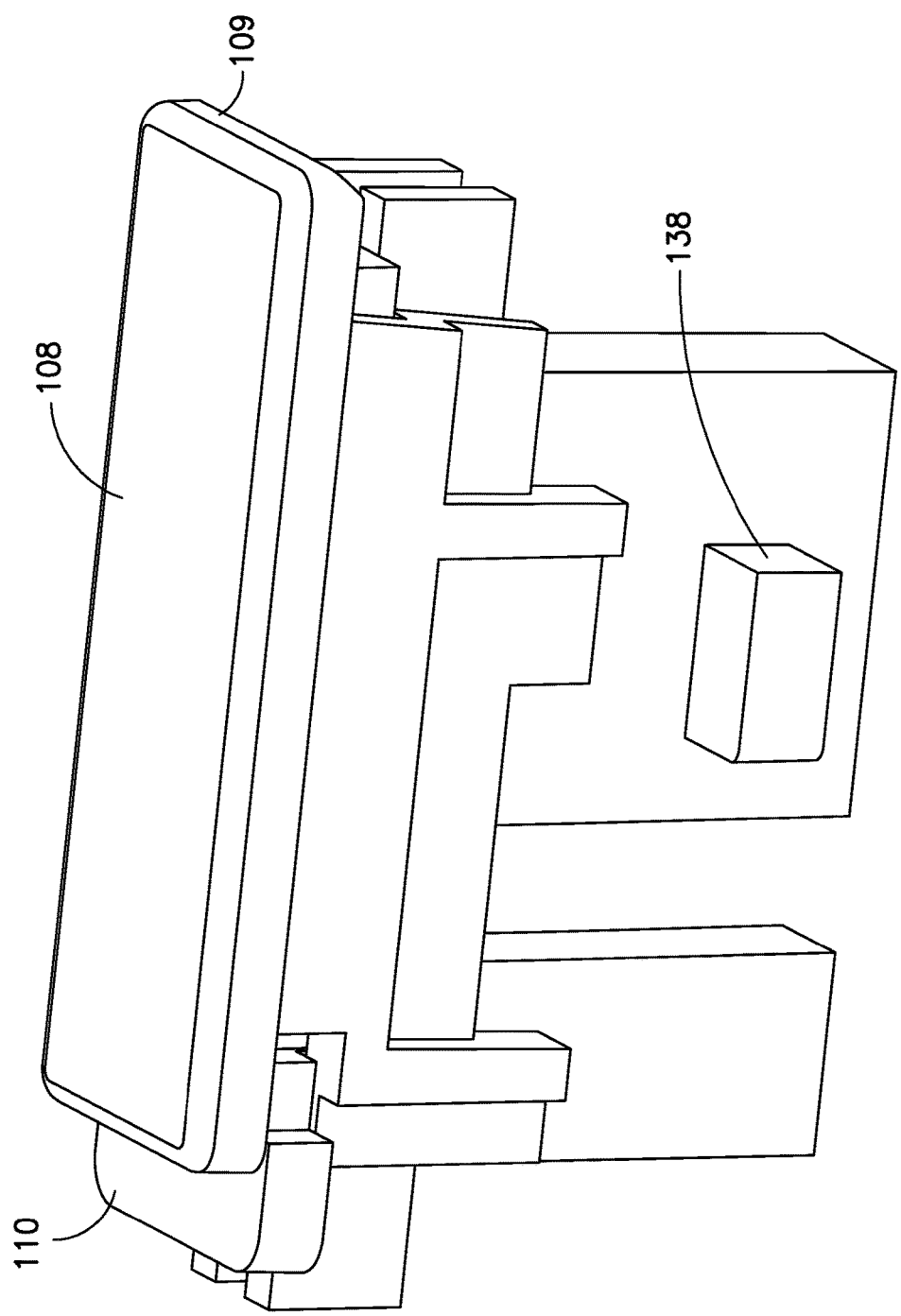
FIG. 4 is a perspective view of a button assembly of the device of FIG. 1.

FIGS. 2 and 3 each have several elements omitted for clarity. Referring to FIGS. 2 and 3, the device 100 includes a needle arm 116 with a port 118 and a patient cannula, such as a needle (not shown) disposed at a free end thereof. The port 118 is connected by tubing (not shown) to a plunger port 120, which is connected to a needle described in greater detail below. The device 100 also includes a needle actuator or slider 122. The progress indicator 114 is connected to the slider 122 and moves distally with the slider 122.

A spring shaft 124 guides a spring 126 that biases the slider 122 distally. The spring 126 bears against a spring pusher 128, which is fixedly connected to the slider 122.

The device 100 also includes an activation flipper 130, a release gate 132, a valve plunger 134, and a release flipper 136. The activation flipper 130 and the release flipper rotate about substantially parallel axes. These axes are substantially perpendicular to the bottom cover 104.

Referring to FIGS. 1-4, to activate the device 100, a user slides the top button portion 108 proximally until it aligns with an opening in the top cover 102. In other words, the user slides the top button portion 108 until a cantilevered portion 109 clears the edge of the opening. Then, the user depresses the top button portion 108 (which also depresses the bottom button portion 110) so that a button protrusion 138 (see FIG. 4) disengages from a first slider protrusion 140 (see FIG. 3), freeing the slider 122 to displace distally under the influence of the spring 126.

As the slider 122 moves distally, an angled portion 144 of the slider 122 rotates the activation flipper 130 about its axis. The slider continues to displace distally under the influence of the spring 126 until a second slider protrusion 142 (see FIG. 3) contacts the release flipper 136 and maintains this position until the dose is delivered, as subsequently described in greater detail. The rotation of the activation flipper 130 causes the release gate 132 to slide laterally and disengage from the valve plunger 134. As subsequently described in greater detail, this frees the valve plunger 134 to move distally under the influence of a plunger spring 146 (see FIG. 5).

In general, in the described embodiments of the device 100, there are two needles for creating a sterile connection with the medicament barrel 106. For example, a large, outer needle or first penetrator 148 creates a hole in two membranes that may each have a non-sterile outer surface. These membranes allow the surfaces inside the respective membranes to remain sterile even if the respective outside membranes may not be sterile. The outer needle 148 creates a hole in each of the (potentially) "contaminated" covers or membranes, which then allows a second penetrator or inner needle 150 to maintain sterility by preventing the inner needle 150 from contacting the non-sterile surfaces.

Figure 5:
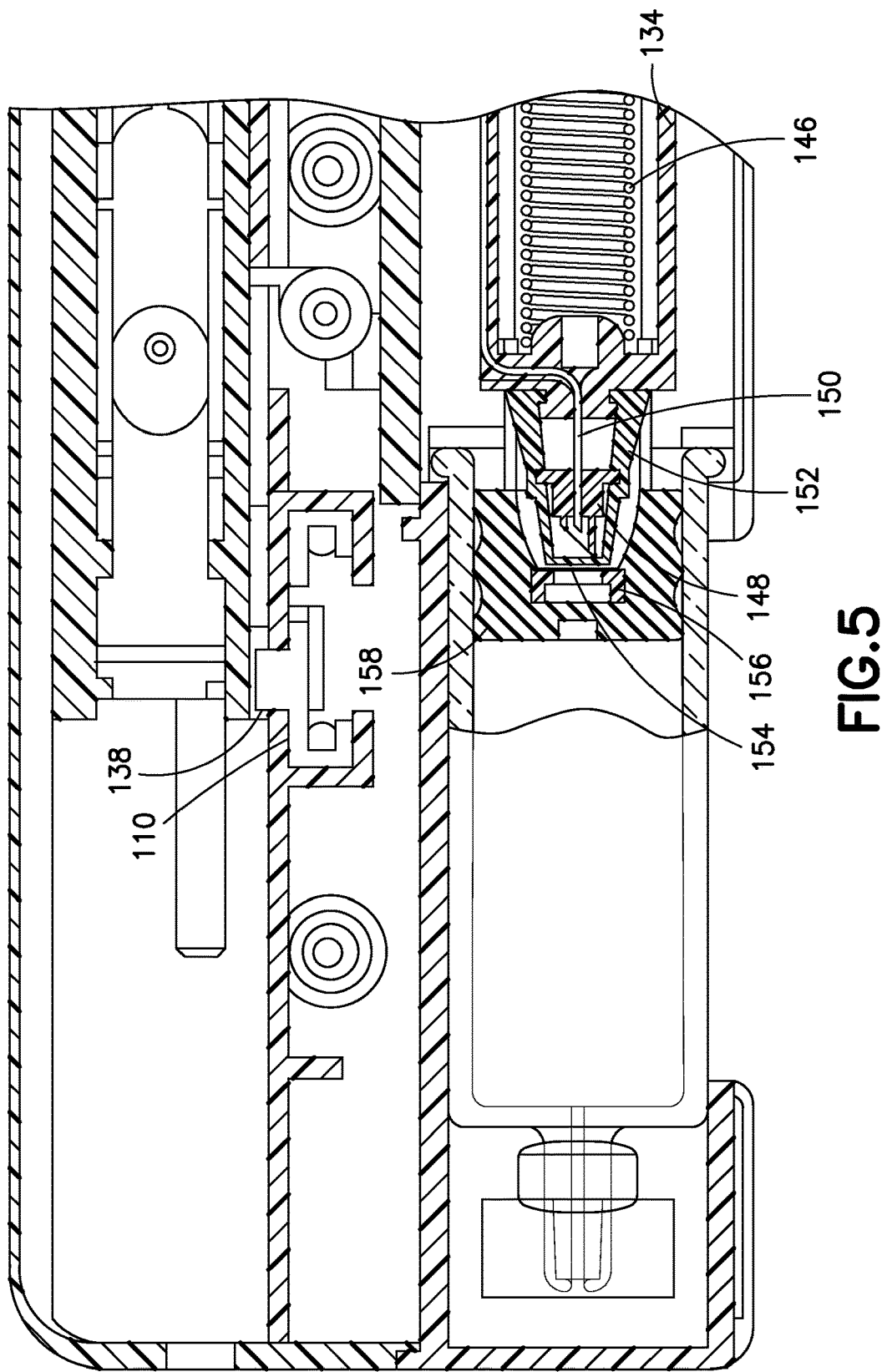
FIG. 5 is a partial cross-sectional view of a double-puncture mechanism in accordance with an embodiment of the present invention.
Figure 6:
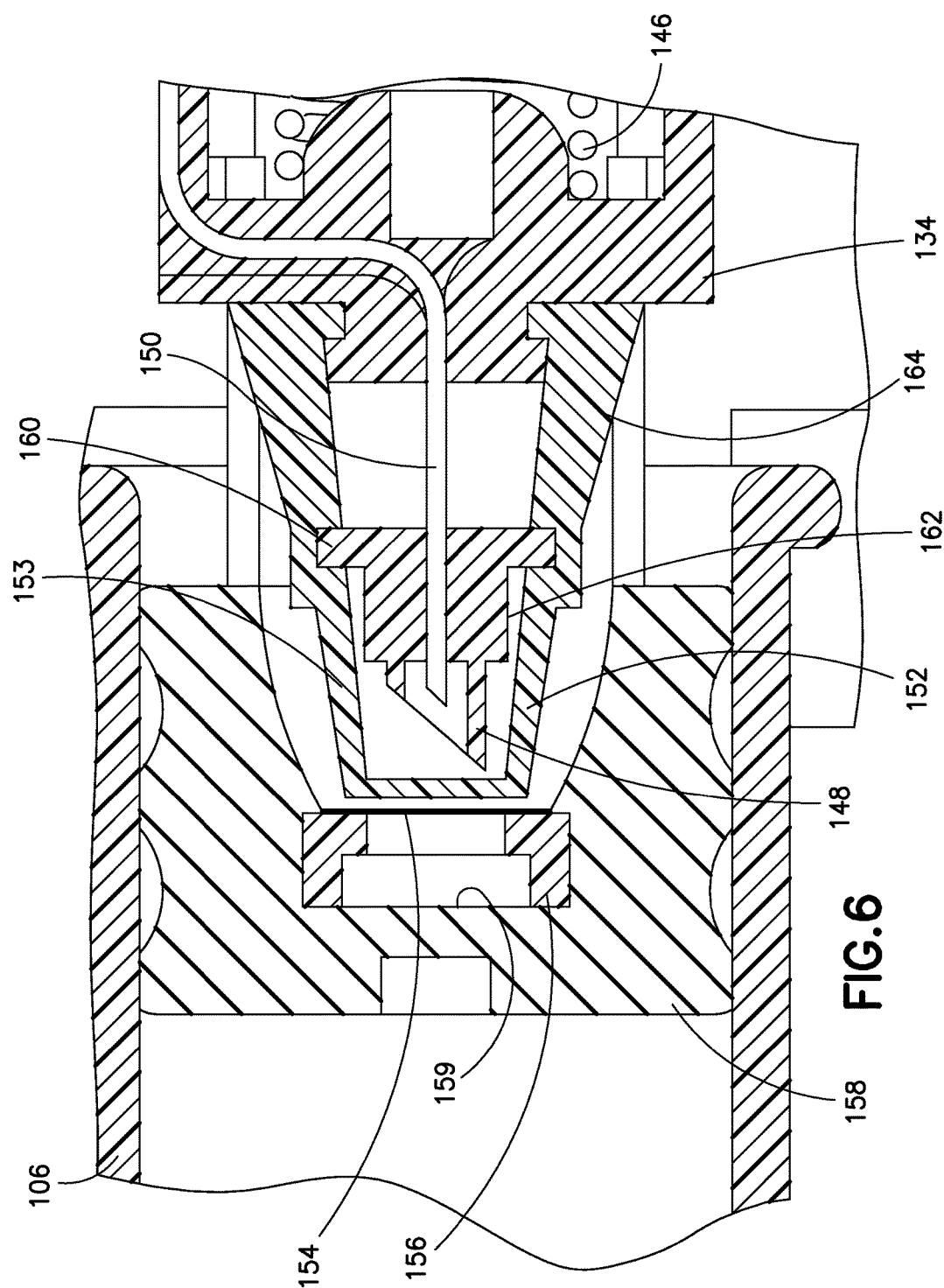
FIG. 6 is an enlarged, partial cross-sectional view of the mechanism of FIG. 5.

More specifically, in the embodiment shown in FIGS. 5 and 6, as the valve plunger 134 displaces distally under the influence of the plunger spring 146, a flexible cover 152 comes into contact with a barrier or membrane 154 disposed on a relatively rigid insert 156 disposed in a stopper 158. With continued distal movement of the valve plunger 134, a front or distal portion 153 of the flexible cover 152 compresses or crumples or collapses. This allows the outer needle 148 to puncture or pierce both a barrier portion of the flexible cover 152 and the membrane 154 without contaminating the inner needle 150. The interior surfaces of the flexible cover 152 and the membrane 154 are sterilized during manufacturing prior to their assembly into the device 100, and remain sterile even though their respective outer surfaces may have become contaminated. Collectively, the flexible cover 152, the first penetrator or outer needle 148, and the second penetrator or inner needle 150 form a valve sleeve assembly.

As the distal displacement of the valve plunger 134 continues an outer flange 160 of the outer needle 148 continues to crumple the distal portion 153 of the flexible cover 152 until the distal progress of the outer needle 148 is halted because an inner flange 162 has a diameter greater than that of the proximal portion of the insert 156. At this point, the valve plunger 134 continues to move distally, and a proximal portion 164 of the flexible cover (which has a thicker wall) begins to compress or crumple. This crumpling of the proximal portion 164 permits the inner needle 150 to distally advance through the bore of the outer needle 148 and contact an interior surface 159 of the stopper 158, which was previously sterilized during manufacture.

The interior surface 159 of the stopper 158 forms a chamber and is covered by the insert 156 and the membrane 154. According to one embodiment, the interior surface 159 is sterilized prior to installation of the insert 156 and the membrane 154. According to another embodiment, the stopper 158, the insert 156, and the membrane 154 are sterilized substantially simultaneously. Subsequent to the stopper's sterilization, the sterility of its proximal end is maintained by the membrane 154. With continued distal movement of the valve plunger 134, the inner needle 150 pierces through the stopper 158 and initiates liquid medicament flow. Continued distal displacement of the valve plunger commences distal displacement of the stopper 158, and the flow of medicament continues (along with distal movement of the valve plunger 134) until the stopper reaches the distal end of the interior of the capped medicament barrel 106.

In this embodiment, the compression or crumpling or collapsing of the flexible cover 152 occurs in two steps; the distal portion 153 of the flexible cover (the area ahead of the outer flange 160 of the outer needle 148) crumples first, allowing the outer needle 148 to pierce both the distal end of the flexible cover 152 and the membrane 154 before the proximal portion 164 crumples. This bifurcated crumpling permits the inner needle 150 to secondarily move forward and pierce the stopper 158. When the device operates in the specified manner, the inner needle 150 will remain sterile without being contaminated.

By permitting two potentially contaminated surfaces to be punctured with the outer needle 148 while maintaining the sterility of the inner needle 150, the pre-filled drug container can be installed into a previously assembled and sterilized infusion device without the need to maintain aseptic conditions until the drug container (e.g., medicament barrel 106)

is installed into the infusion device. This allows the pre-filled drug container to be assembled by a pharmaceutical company or an end user without requiring the assembly environment to be aseptic. In addition, this permits the pre-filled medicament barrel 106 to be filled and inspected using industry-standard equipment and methods.

Figure 7:
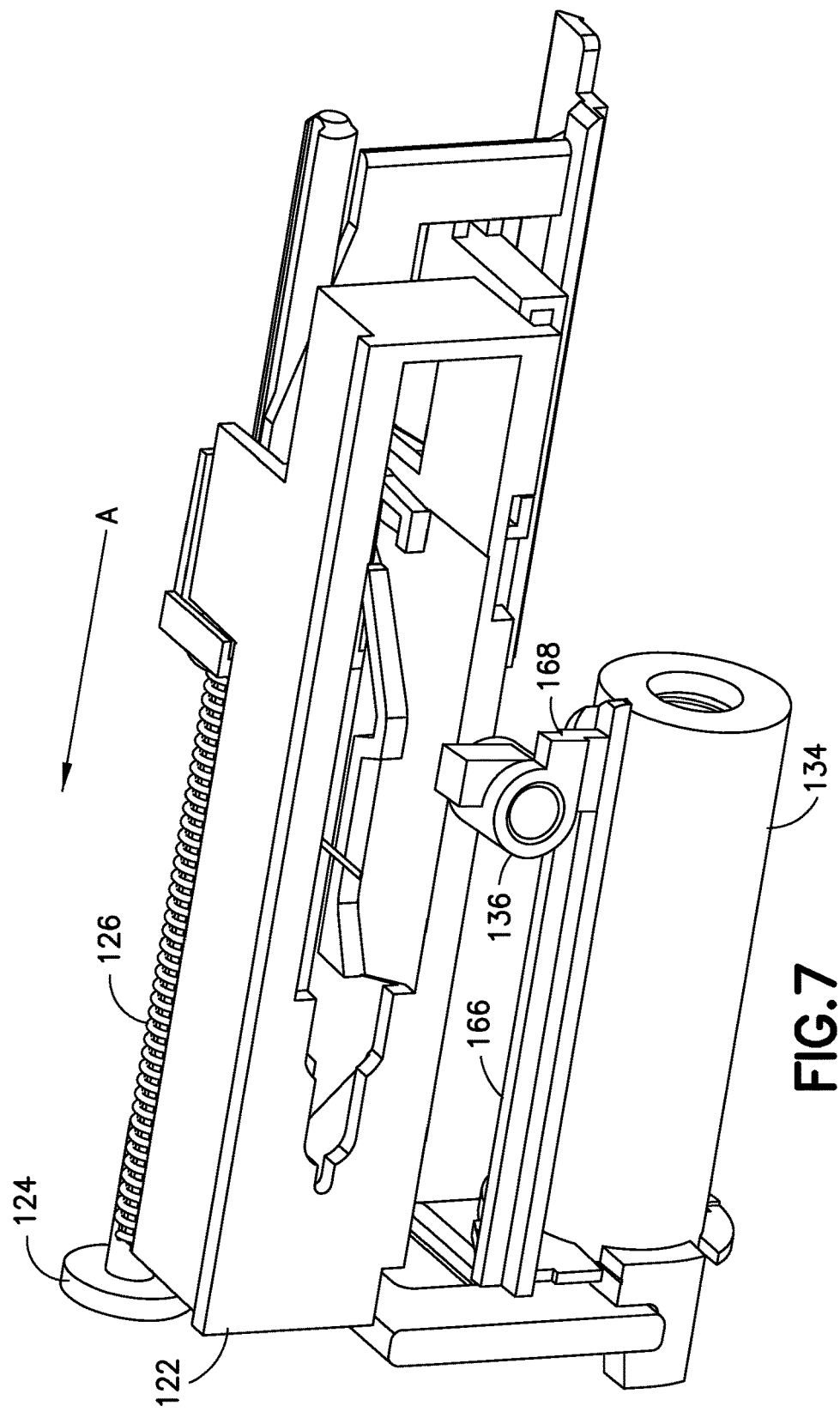
FIG. 7 is a bottom perspective view of another double-puncture mechanism in accordance with an embodiment of the present invention.

FIG. 7 is a bottom perspective view of portions of the device 100, in which the slider 122 is shown as being transparent for clarity. One skilled in the art will appreciate that the opacity of the slider 122 can vary without departing from the present invention's scope. Referring to FIGS. 2 and 7, the valve plunger 134 has a cantilevered arm 166 with a vertical portion and a horizontal portion on its underside. These vertical and horizontal portions form a guide for a lower arm 168 of the release flipper 136. The contact between the guide and the lower arm 168 prevents rotation of the release flipper 136.

As the valve plunger 134 finishes its distal travel to end flow of the medicament, the proximal end of the cantilevered arm 166 bypasses the lower arm 168, thereby freeing the release flipper 136 to rotate because of the contact of the second slider protrusion 142 (see FIG. 3) with an upper arm 170 (see FIG. 3) of the release flipper 136 and the continued bias of the spring 126. Once the release flipper 136 rotates sufficiently that the second slider protrusion 142 bypasses the upper arm 170 of the release flipper 136, the slider 122 continues its distal displacement. Because of contact of wings 119 at the proximal end of the needle arm 116 with a ramp 125 of a track on the interior of the slider 122, the continued distal displacement of the slider raises the proximal end of the needle arm 116 and withdraws the patient cannula (not shown). The continued distal displacement of the slider 122 also distally displaces the progress indicator 114, so that the user can see that the dosage is complete through the indicator window 112.

Figure 8:
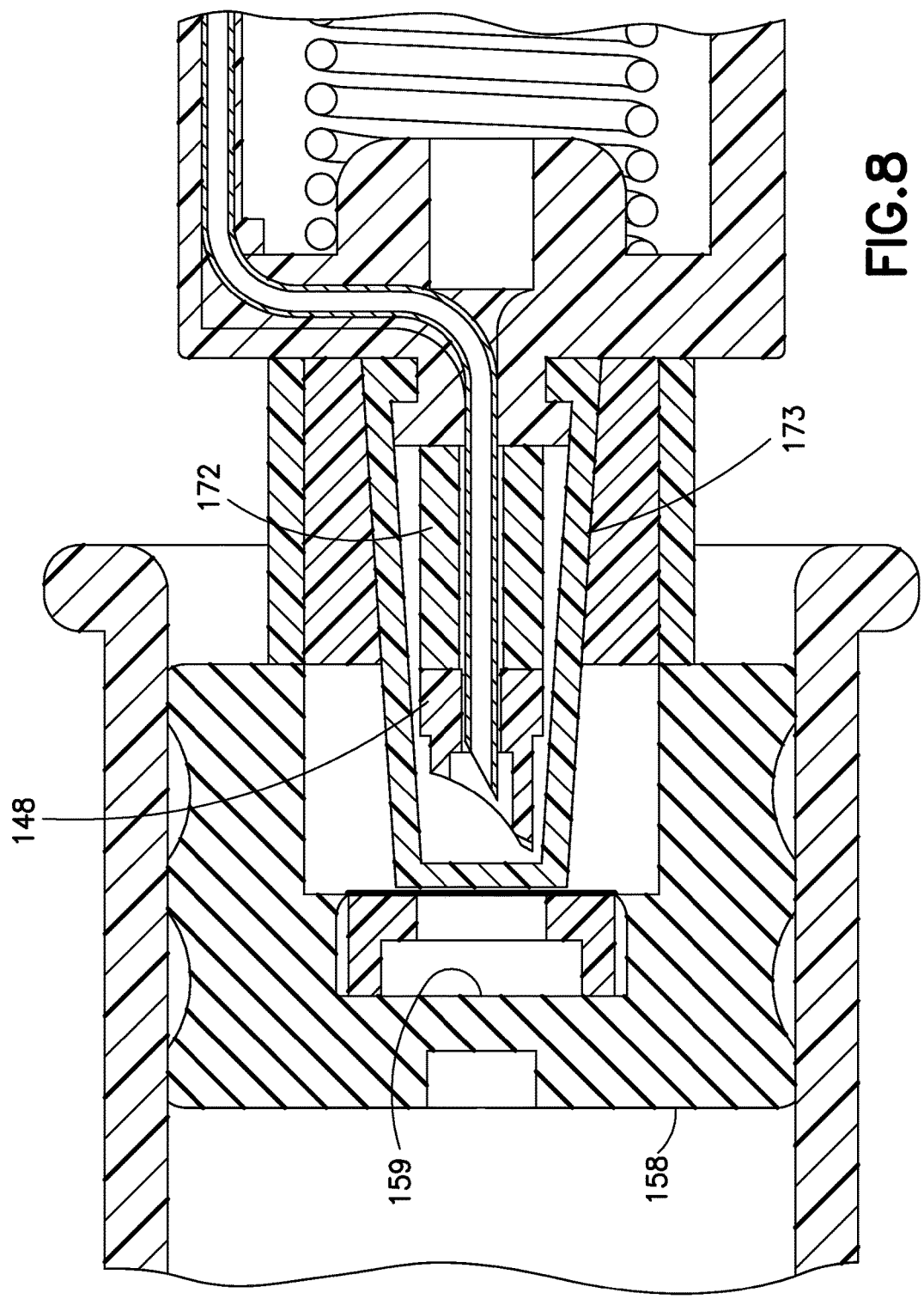
FIG. 8 is a partial cross-sectional view of another double-puncture mechanism in accordance with an embodiment of the present invention.

In an alternative double puncture embodiment in FIG. 8, the wall thickness of the flexible cover 173 is substantially constant. In this embodiment, a two-shot molded part 172 acts as an elastomeric "spring" that is molded to the back of the outer needle 148. As in the embodiment of FIGS. 5 and 6, the outer needle 148 pierces the two sterile barriers before the inner needle proceeds forward into the sterile wall 159 of the septum 158. In concert with the crumpling of the flexible cover 173, the elastomeric "spring" 172 provides the effect of the bifurcated crumpling of the embodiment in FIGS. 5 and 6, that is, the piercing by the outer needle 148 and the displacement of the inner needle 150 relative to the outer needle 148.

Figure 9:
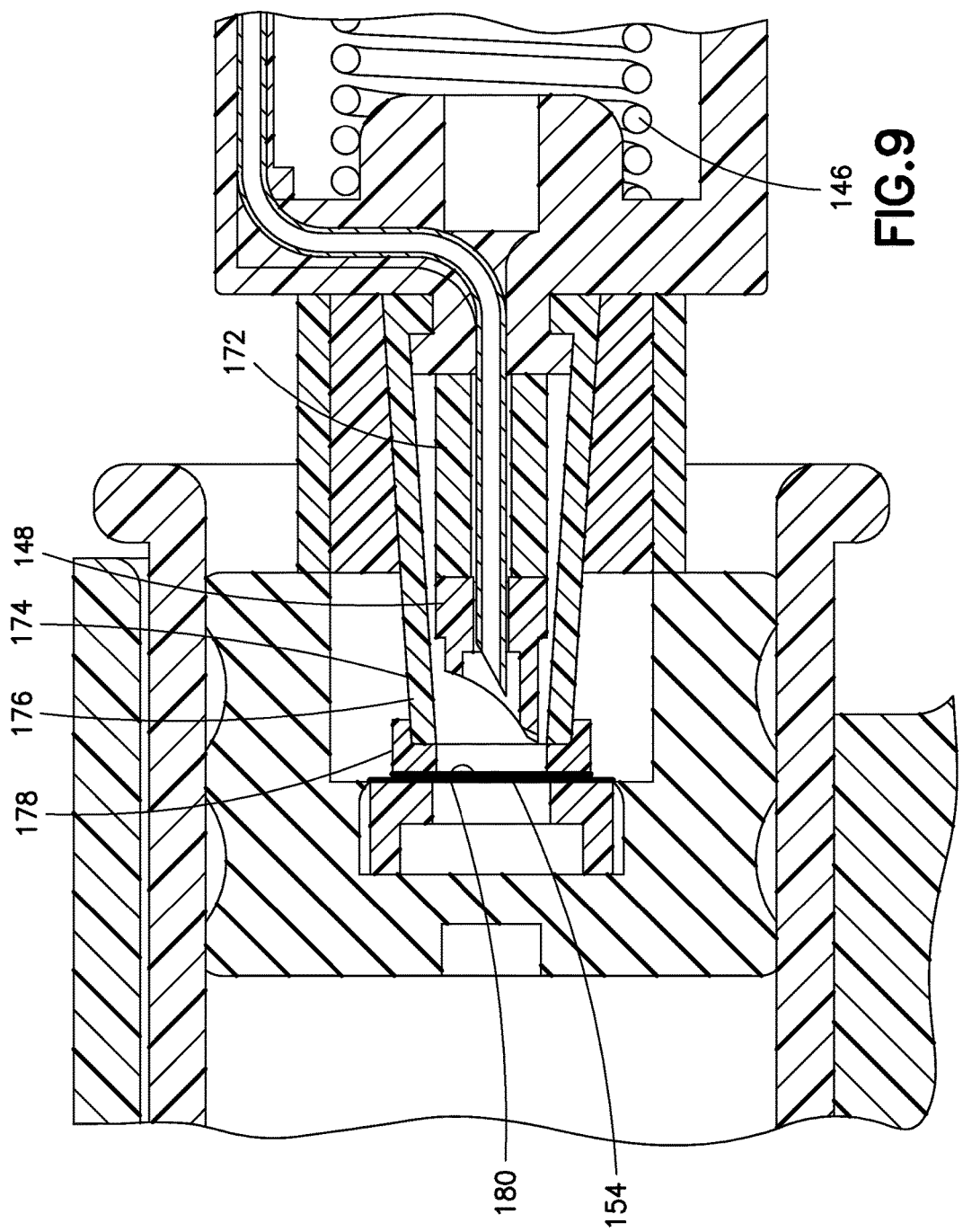
FIG. 9 is a partial cross-sectional view of another double-puncture mechanism in accordance with an embodiment of the present invention.

In another alternative embodiment in FIG. 9, the flexible cover 174 is a two-shot molded part, and has a crumpling portion 176 and a distal portion 178. The distal portion 178 has a membrane 180 sealed to the end of the distal portion. As shown in FIG. 9, the membrane 180 and the membrane 154 abut each other prior to either membrane being pierced by the outer needle 148. The spacing between the two membranes 180, 154, however, can vary without departing from to the present invention's scope. For example, the two membranes 180, 154, can be spaced apart or in full contact. The spacing of the two membranes affects the length and/or the travel of the outer needle 148 because the outer needle 148 pierces both membranes 180, 154. Preferably, the space between the two membranes 180, 154 is minimized, or the membranes are in contact.

In this embodiment, rather than having to pierce the material that the remainder of the flexible cover 174 is made of (for example, rubber, or an elastomer, such as a medical-grade plastic), the outer needle 148 only needs to pierce the membrane(s) 180, 154. Accordingly, the force required to be produced by the spring 146 is reduced.

Figure 10:
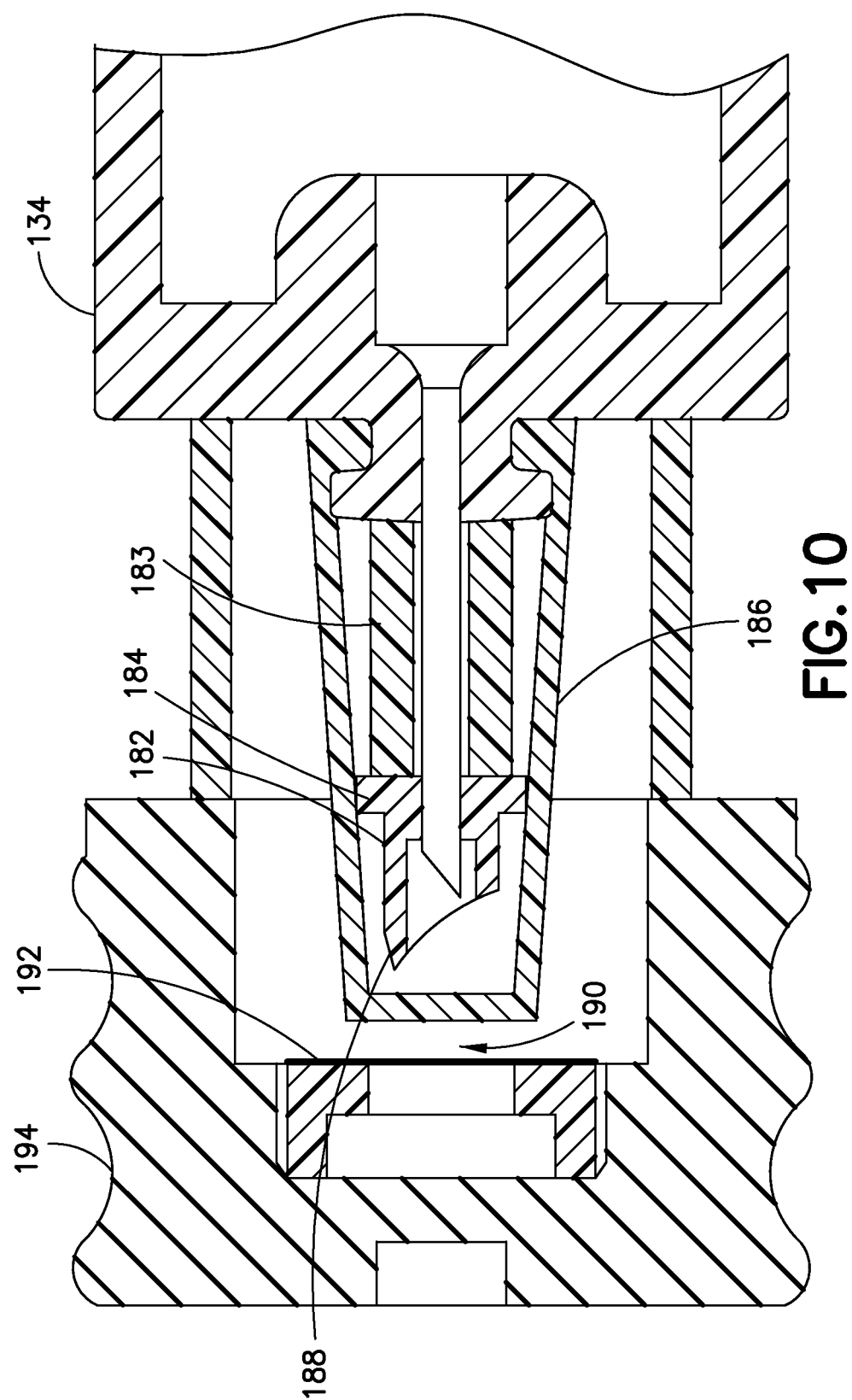
FIG. 10 is a partial cross-sectional view of the double-puncture mechanism in accordance with the embodiment of FIG. 8.

Like the embodiments of FIGS. 8 and 9, in the embodiment in FIG. 10, the outer needle 182 is also connected to the elastomeric "spring" 183. In contrast, however, the proximal flange 184 of the outer needle 182 extends radially farther outward than the embodiments of FIGS. 8 and 9. According to one embodiment, the proximal flange 184 contacts the interior of the flexible cover 186. Additionally, the distal end of the outer needle includes one or more facets 188 to optimize the piercing ability of the outer needle 182.

Moreover, in contrast to previously-described embodiments, there is a greater space 190 between the distal end of the flexible cover 186 and the membrane 192 disposed at the proximal end of the stopper 194 prior to distal displacement of the valve plunger 134. According to one embodiment, an antiseptic material is disposed in the space 190.

Figure 11:
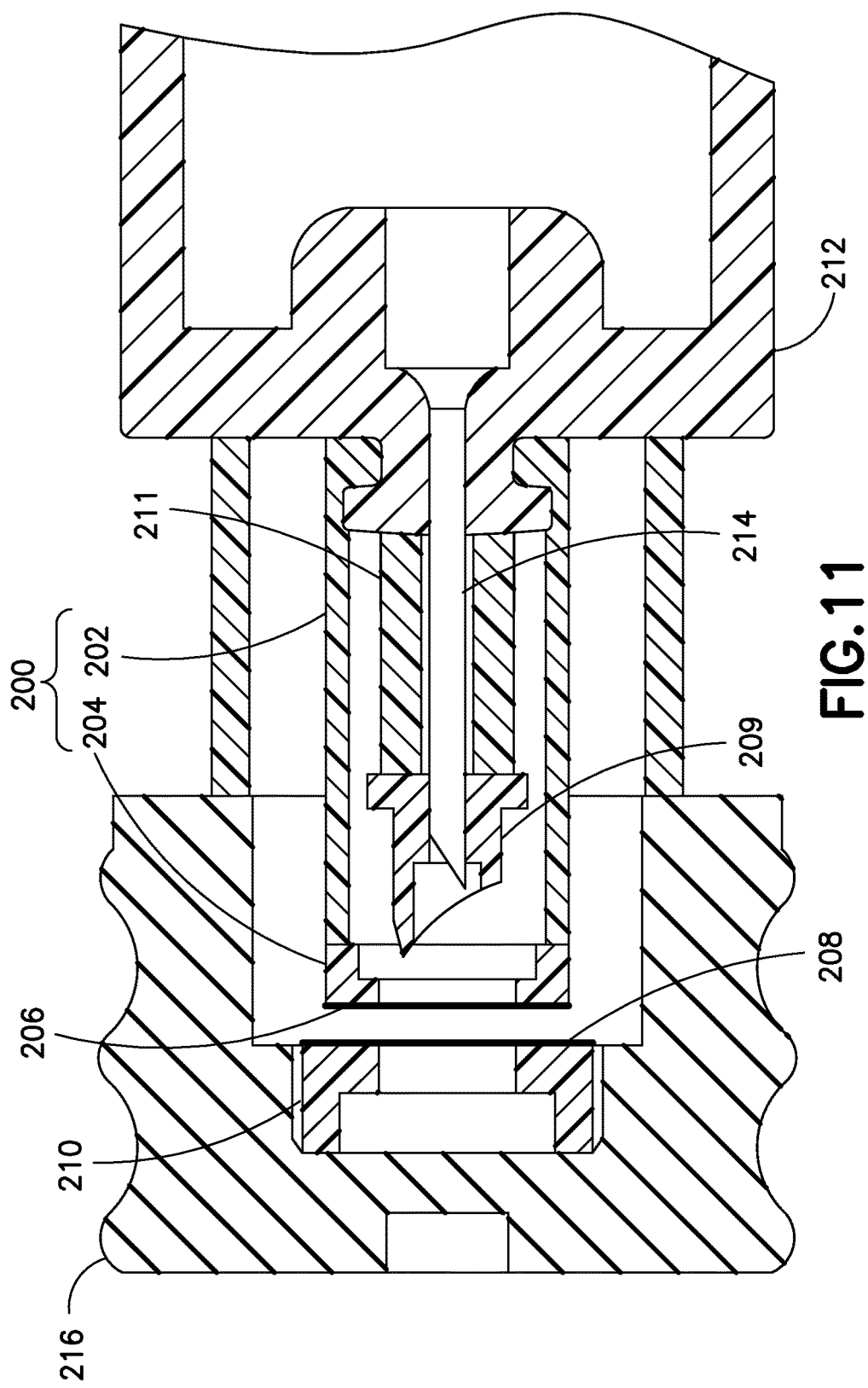
FIG. 11 is a partial cross-sectional view of another double-puncture mechanism in accordance with an embodiment of the present invention.

Similar to the embodiment of FIG. 9 in many respects, the embodiment shown in FIG. 11 includes a flexible cover 200, which is made using a two-shot molding process. A proximal cover portion 202 is collapsible as previously described, and a distal cover portion 204 is joined to the proximal cover portion 202. A membrane 206 is disposed across a distal opening in the distal cover potion 204. In addition, a membrane 208 is disposed across a proximal end of a stopper insert 210. Material choices for the membranes 206 and 208 (and other previously-described membranes) include a thin foil, or plastic films.

Briefly, in operation, the outer needle or penetrator or inserter 209 opens a sterile path for the inner needle 214 and then the inner needle 214 moves through the sterile path and punctures the stopper 216. In greater detail, as shown in the left side of FIG. 12, the outer needle or penetrator 209, which is disposed on the distal end of a rubber spring 211, first penetrates both of the membranes 206 and 208 during distal displacement of the valve plunger 212. Then, as shown in the right side of FIG. 12, the sterile inner needle 214 penetrates the stopper 216 to form the sterile connection with the medicament disposed within the medicament barrel 106.

Like the embodiment of FIGS. 11 and 12, the subsequently-described embodiments of FIGS. 13-16 include a flexible cover having a membrane covering a distal opening thereof.

Figure 13:
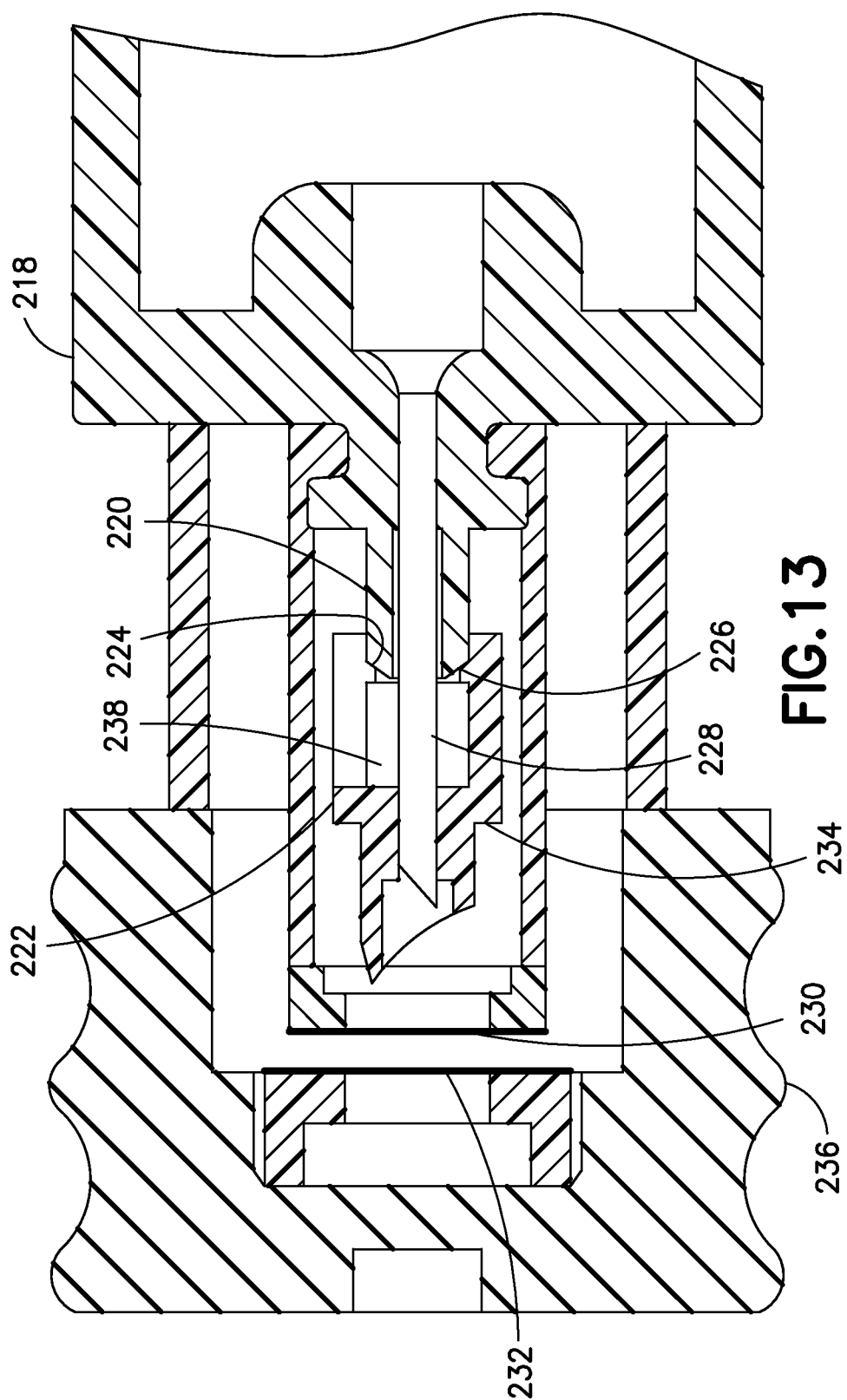
FIG. 13 is a partial cross-sectional view of another double-puncture mechanism in accordance with an embodiment of the present invention.

In the embodiment shown in FIG. 13, the valve plunger 218 has a distal protrusion 220 to which the inner needle 228 is fixedly connected. The distal protrusion 220 contacts a proximal portion of the outer needle 222. The proximal portion of the outer needle 222 has a detent 224 with a shape that corresponds to a distal end 226 of the valve plunger's distal protrusion 220. The interaction of the detent 224 and the distal end 226 controls the force of collapse. For example, the shape, the rigidity, and/or the fit between the detent 224 and the distal end 226 can affect the amount of force needed for the distal end 226 to displace relative to the detent 224. According to one embodiment, the detent 224 and the distal end 226 are slanted.

In operation, the valve plunger 218 and the outer needle 222 initially both displace distally without displacing relative to each other. This simultaneous but non-relative displacement continues until the outer needle 222 pierces the membranes 230 and 232 and the outer needle's proximal flange 234 prevents further displacement of the outer needle 222 relative to the stopper 236. Upon continued distal displacement of the valve plunger 218, the distal end 226 disengages from the detent 224, and the valve plunger 218 and the inner needle 228 displace distally relative to the outer needle 222 (and the stopper 236). During this continued distal displacement, the distal end 226 travels into a cavity 238 on the interior of the outer needle 222, and the inner needle 228 pierces the stopper 236 to form a sterile connection with the medicament disposed within the medicament barrel 106.

Figure 14:
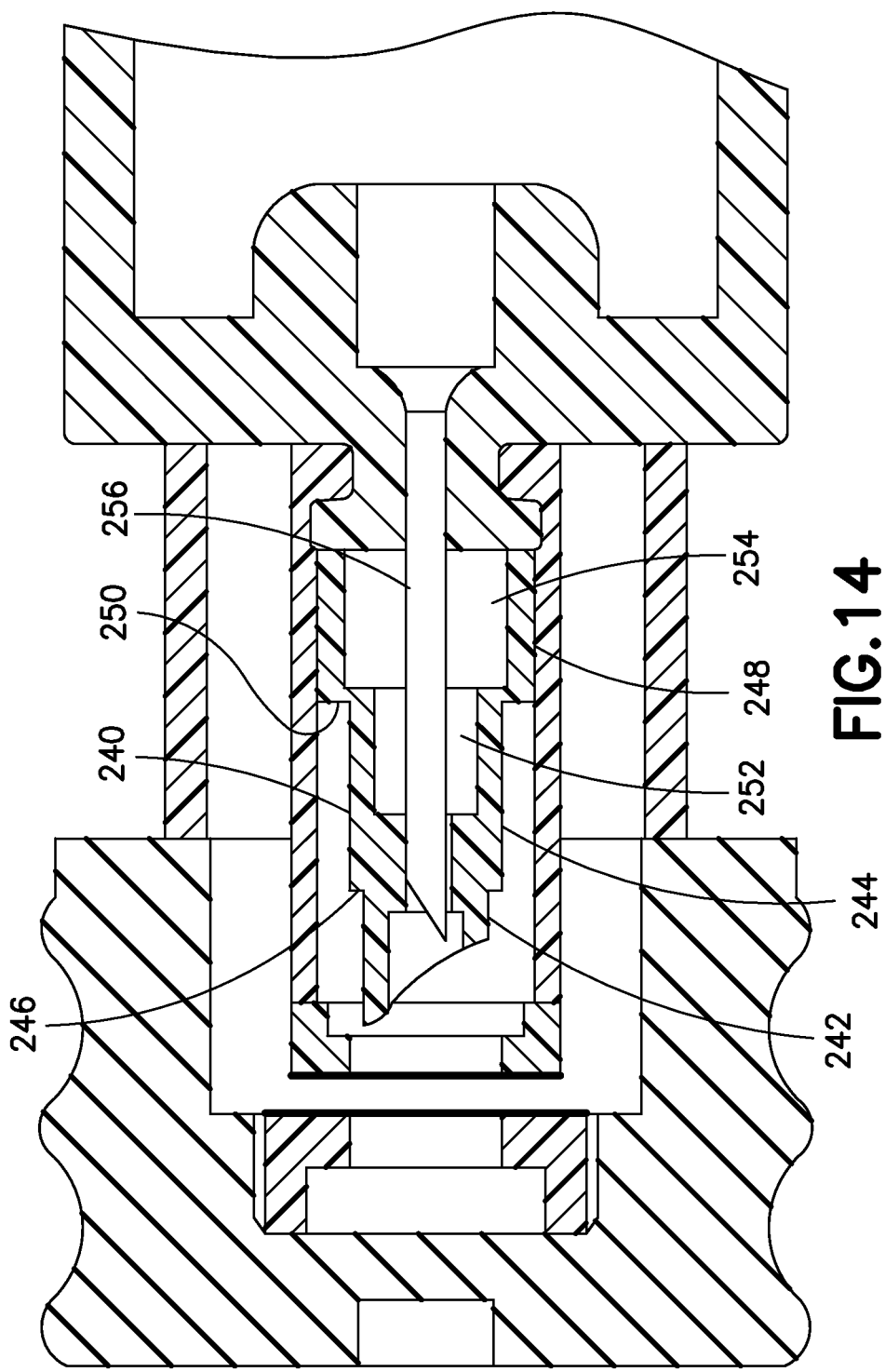
FIG. 14 is a partial cross-sectional view of another double-puncture mechanism in accordance with an embodiment of the present invention.

In the embodiment in FIG. 14, the outer needle or penetrator 240 has a geometry designed to control its collapse during the penetration sequence. More specifically, the outer needle 240 has a distal penetrating portion 242, a central portion 244 with a first flange 246 at its distal end, and a proximal portion 248 with a second flange 250 at its distal end. The central portion 244 includes a central void 252, and the proximal portion 248 includes a proximal void 254. The combination of the lengths, outer diameters, and wall thicknesses of the central and proximal portions 244 and 248, along with the volumes of the central and proximal voids 252 and 254 provides a controlled collapse of the outer needle 240, to define the timing of the distal displacement of the inner needle 256 relative to the outer needle 240.

Figure 15:
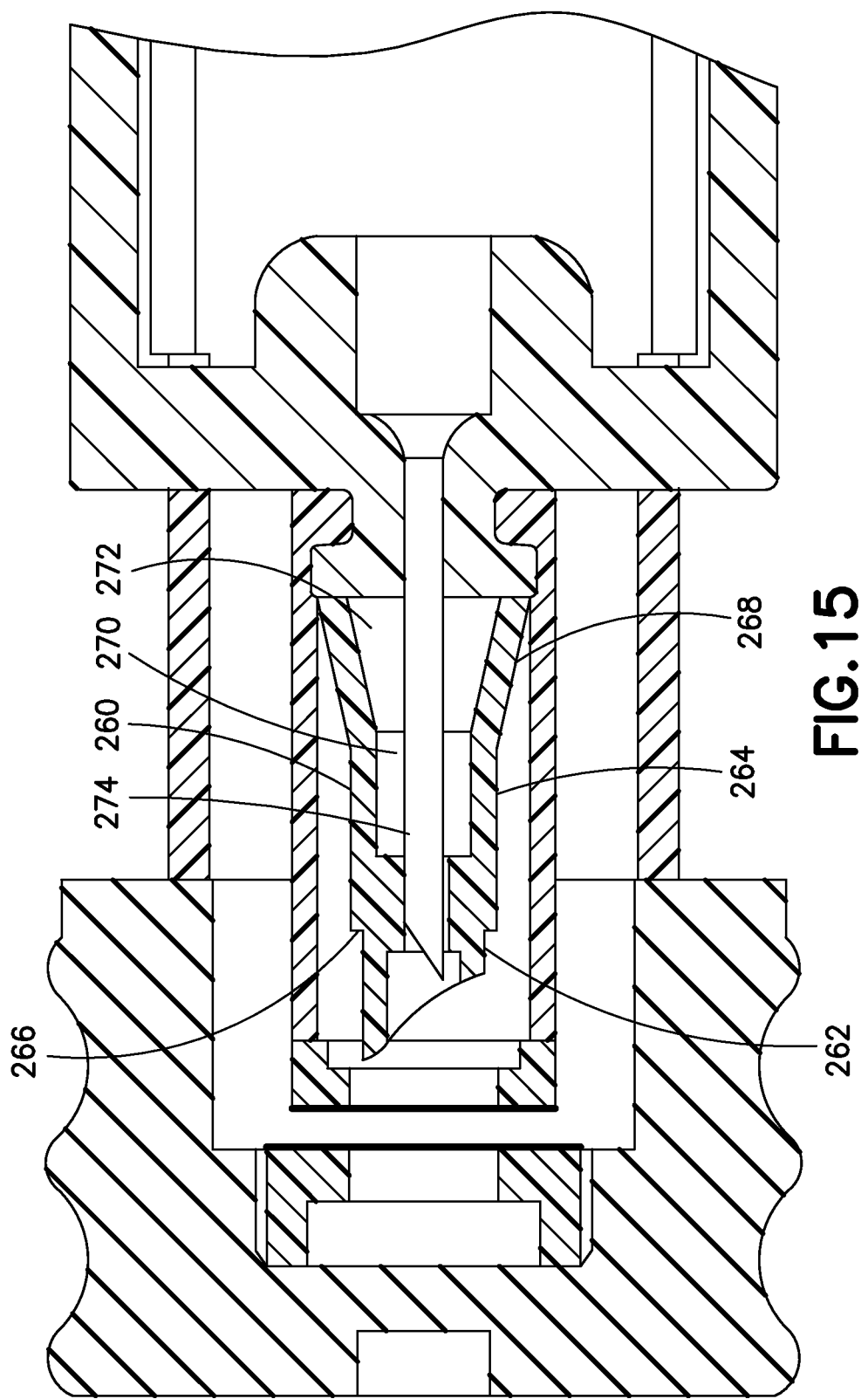
FIG. 15 is a partial cross-sectional view of another double-puncture mechanism in accordance with an embodiment of the present invention.

Similarly, in the embodiment shown in FIG. 15, the outer needle or penetrator 260 includes a distal penetrating portion 262, a central portion 264 with a flange 266 at its distal end, and a proximal portion 268. In contrast to the proximal portion 248 of the embodiment of FIG. 14, which is substantially cylindrical, the proximal portion 268 tapers to have an increased diameter at its proximal end. The central portion 264 has a central void 270 and the proximal portion 268 has a proximal void 272. The combination of the lengths and wall thicknesses of the central and proximal portions 264 and 268, along with the taper angle of the proximal portion 268 and the volumes of the central and proximal voids 270 and 272 provides a controlled collapse of the outer needle 260, to define the timing of the distal displacement of the inner needle 274 relative to the outer needle 260.

Figure 16:
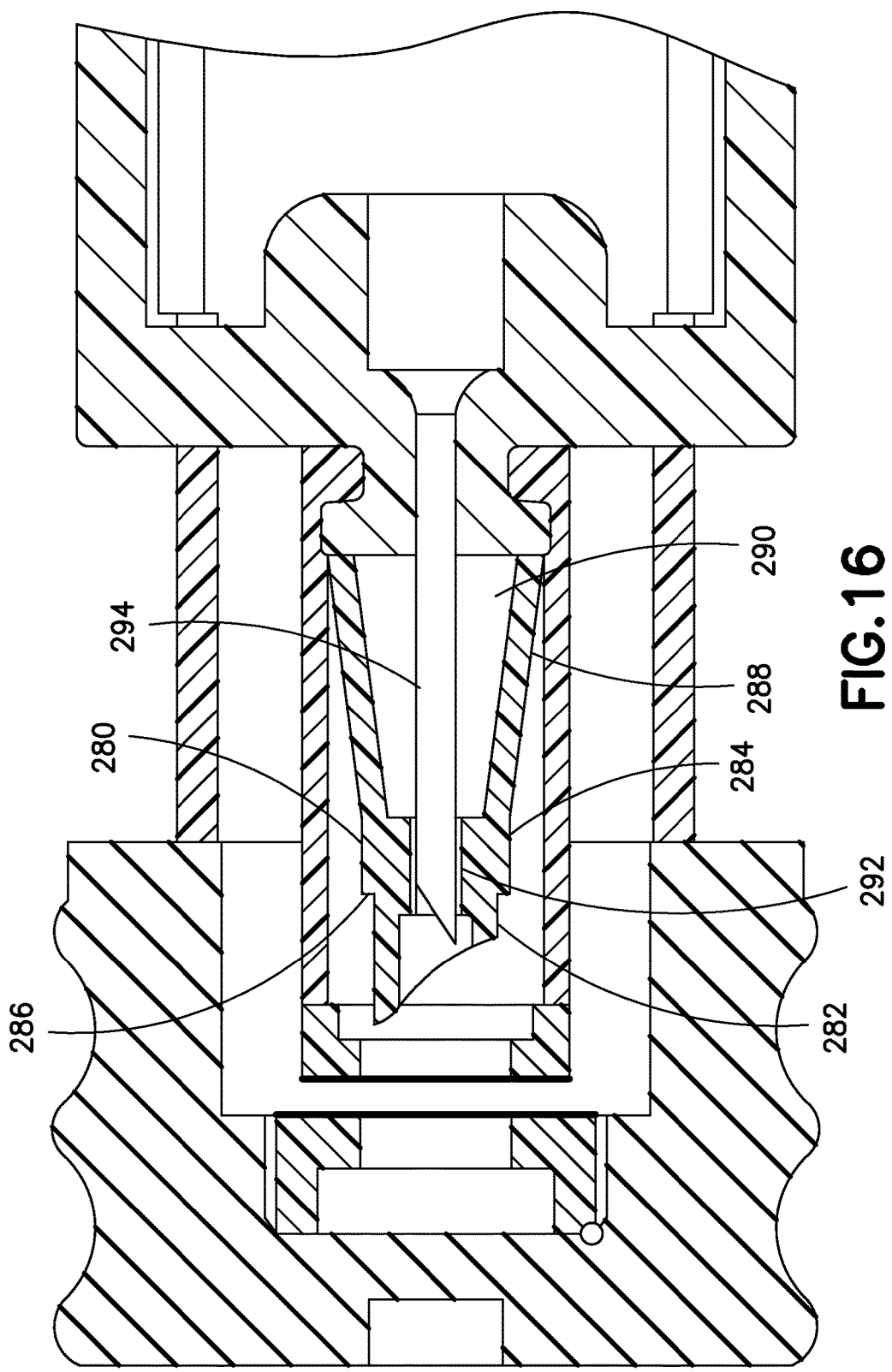
FIG. 16 is a partial cross-sectional view of another double-puncture mechanism in accordance with an embodiment of the present invention.

In the embodiment shown in FIG. 16, similar to the embodiment shown in FIG. 15, the outer needle or penetrator 280 includes a distal penetrating portion 282, a central portion 284 with a flange 286 at its distal end, and a proximal portion 288 that tapers to have an increased diameter at its proximal end. The tapered proximal portion 288 includes a proximal void 290. In contrast to the embodiment of FIG. 15, however, except for a central passage 292 for the inner needle 294, the central portion 284 is substantially solid. In addition, compared to the embodiments of FIGS. 14 and 15, the length of the central portion 284 is decreased and the length of the proximal portion 288 is increased. The combination of the length, wall thickness, and taper angle of the proximal portion 288, along with the volume of the proximal void 290 provides a controlled collapse of the proximal portion 288 of the outer needle 280, to define the timing of the distal displacement of the inner needle 294 relative to the outer needle 280.

Although not shown, the embodiments of FIGS. 14-16 can optionally include in-molded springs disposed on the respective proximal ends of the outer needles 240, 260, and 280. Although also not shown, the embodiments of FIGS. 14-16 can optionally include lever arms disposed on the respective proximal ends of the outer needles 240, 260, and 280.

Material choices for the outer needle or penetrator in embodiments of the present invention include metal, such as surgical stainless steel, and rigid plastic, such as polypropylene.

Figure 17:
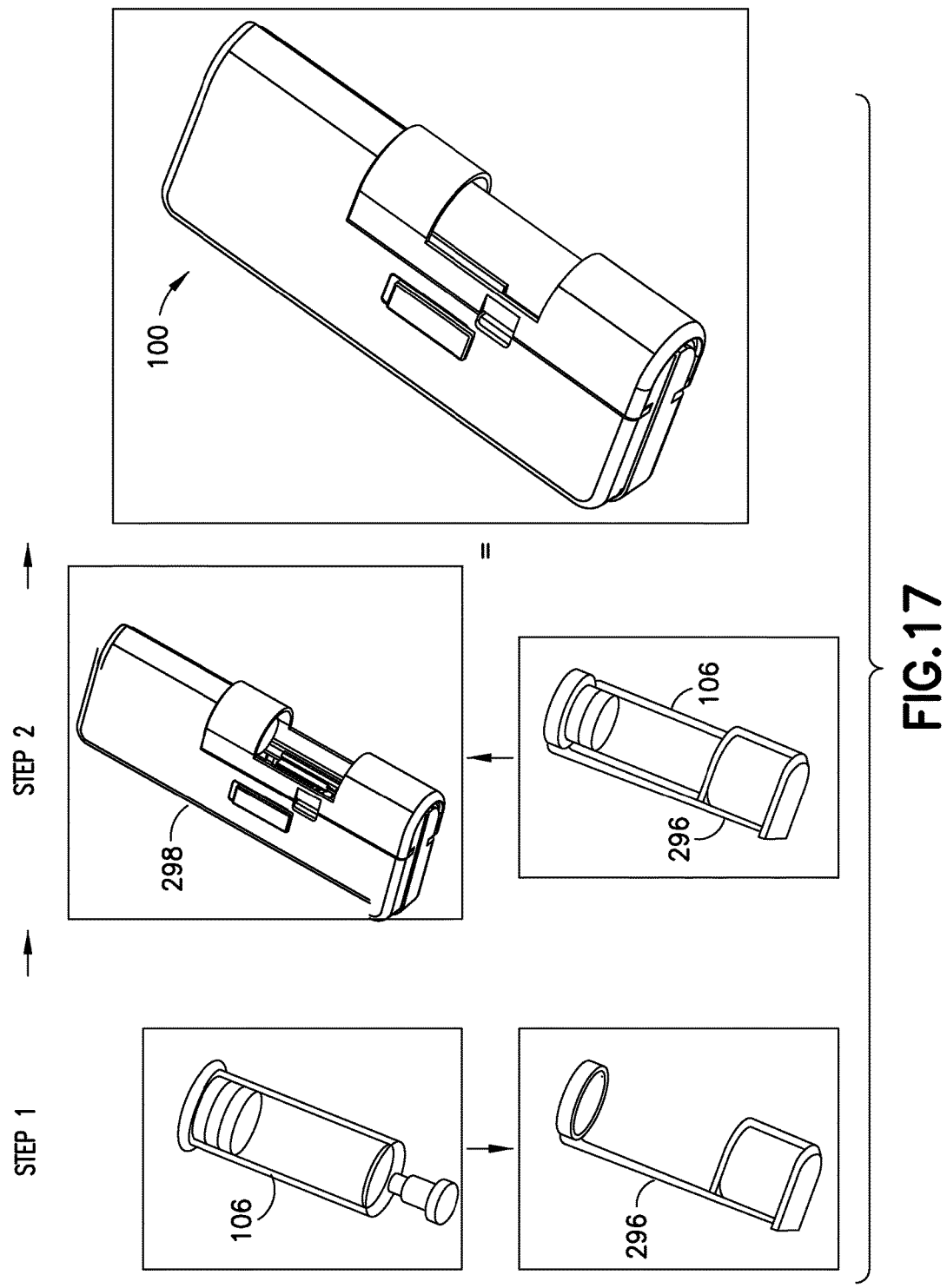
FIG. 17 illustrates a method of inserting a medicament barrel into a body of the device of FIG. 1.

FIG. 17 illustrates a method of inserting the medicament barrel 106 into a body 298 of the device 100. As shown on the left side of FIG. 17, initially, a user inserts the medicament barrel 106 into a holder 296. Preferably, barrel 106 has been aseptically filled with medicament prior to insertion. Subsequently, as shown in the middle of FIG. 17, the user then inserts the combined medicament barrel 106 and holder 196 into the body 298, thereby readying the device 100 for use. Optionally the holder is omitted and the barrel 106 is inserted directly into body 298 of device 100.

Figure 18:
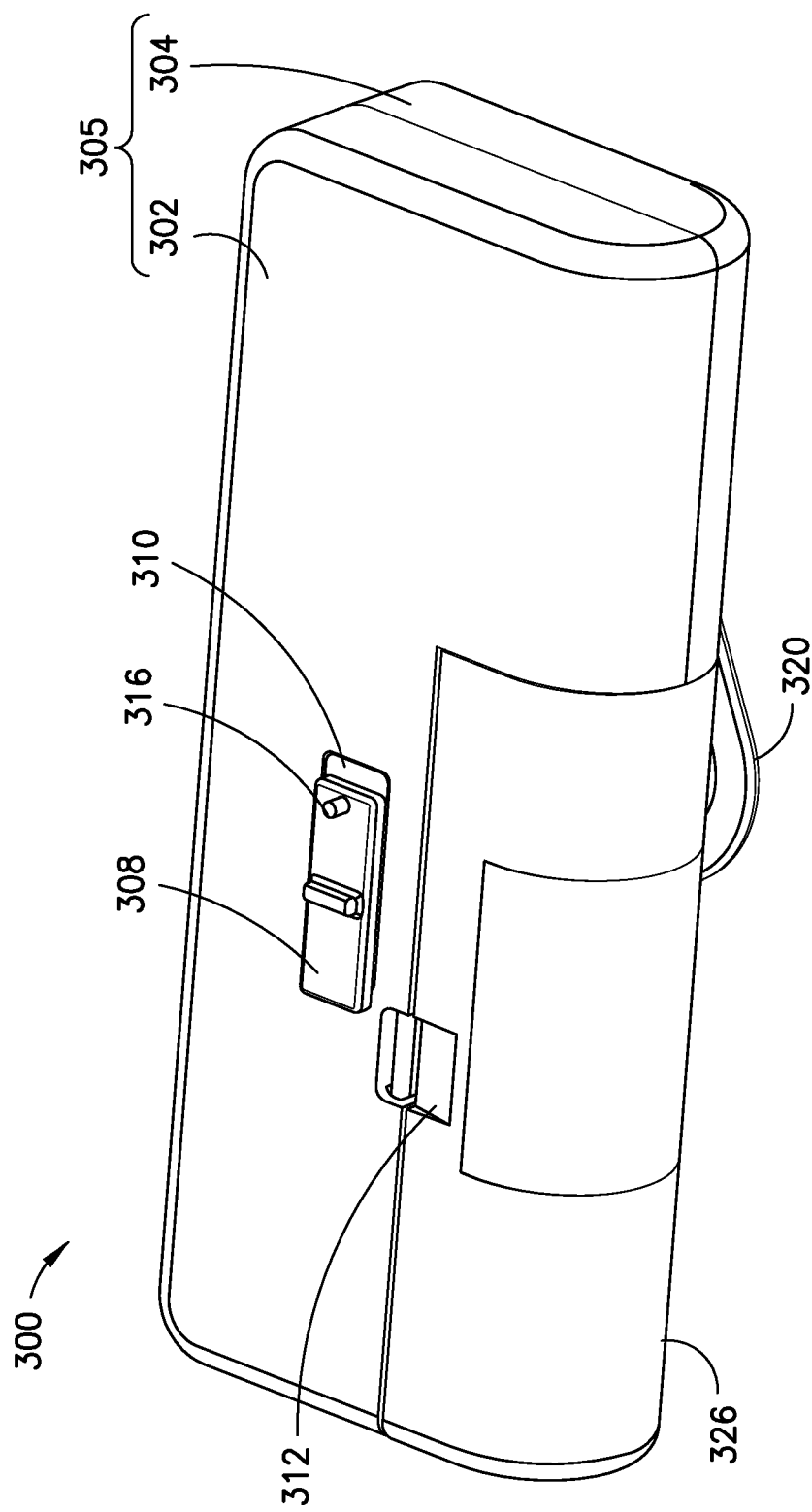
FIG. 18 is a top perspective view of an infusion device in accordance with an embodiment of the present invention.
Figure 19:
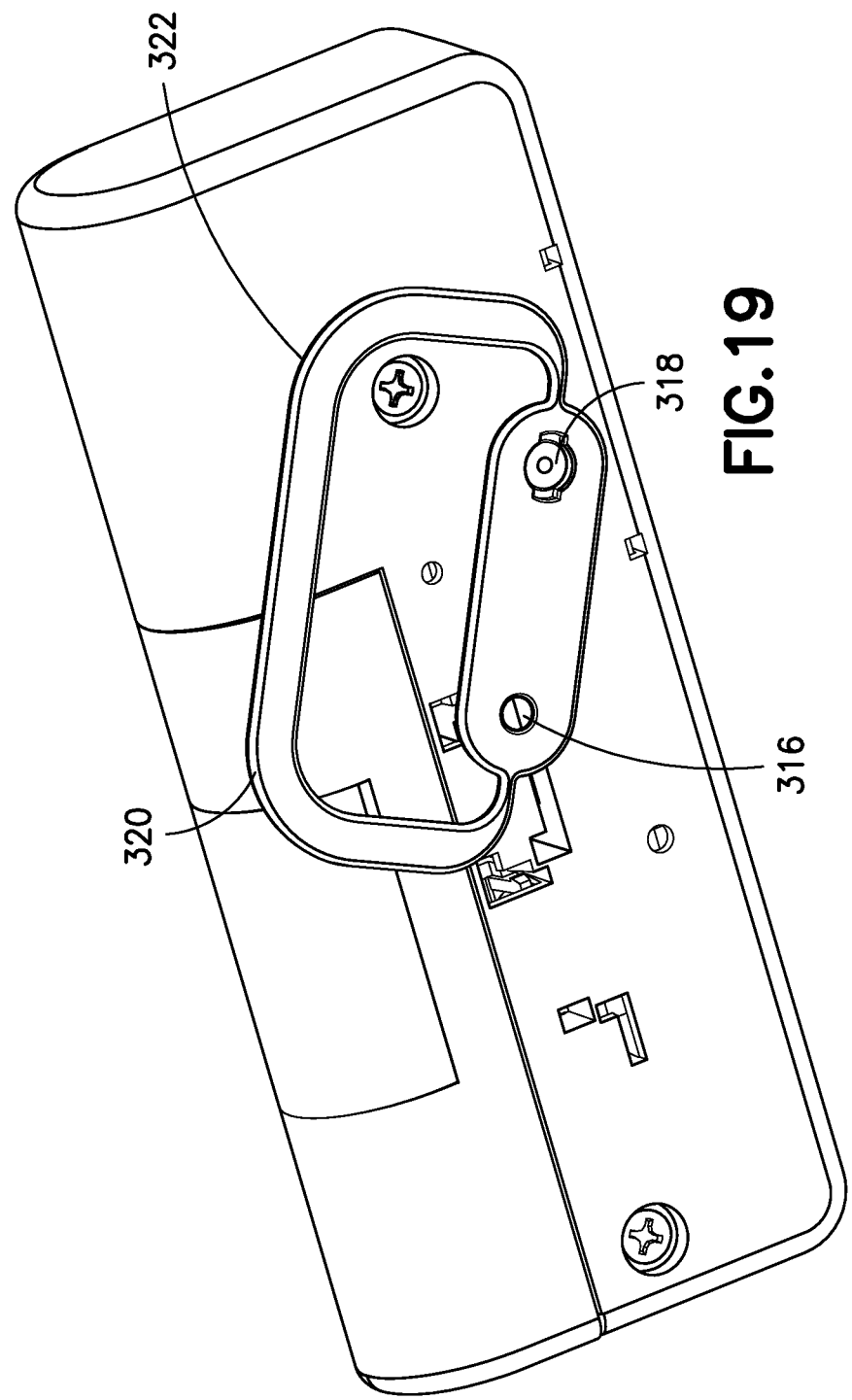
FIG. 19 is a bottom perspective view of the infusion device of FIG. 18.
Figure 20:
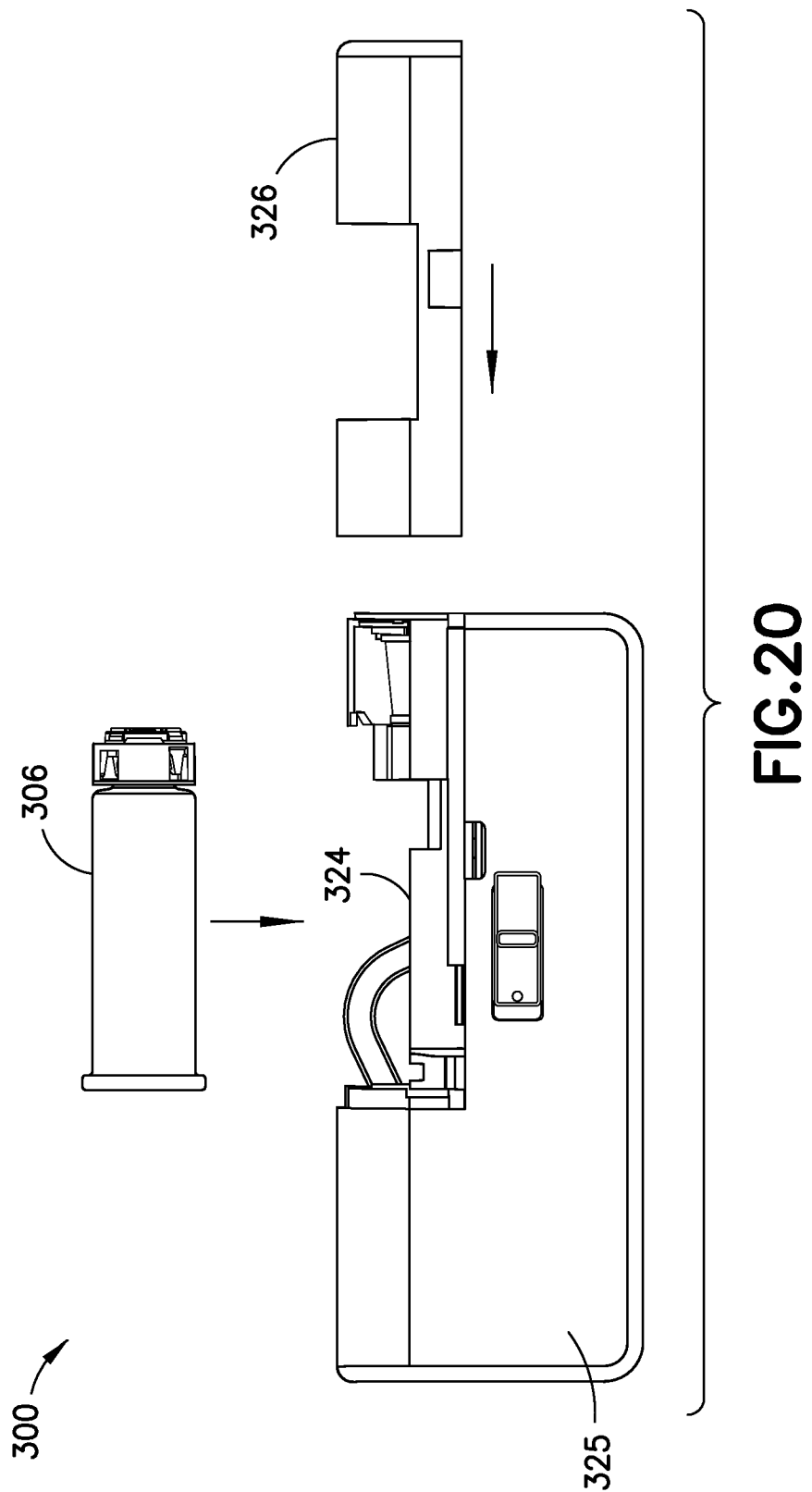
FIG. 20 illustrates a method of inserting a medicament barrel into a body of the device of FIG. 18.

FIGS. 18 and 19 are perspective top and bottom perspective views of an infusion device 300 in accordance with another embodiment of the present invention, and FIG. 20 illustrates a method of inserting a medicament barrel into a body of the device 300. In many respects, the device 300 is similar to the device 100 previously described. For example, the device 300 includes a top cover 302, a bottom cover 304 (which together form a device body 305), a medicament barrel 306, a top button portion 308, a bottom button portion 310, and an indicator window 312, through which the user can see a progress indicator 314 to aid in determining the completion of the dose. For brevity, aspects of the device 300 substantially similar to those of the device 100 will not be described in great detail.

But in contrast to the device 100 in which the valve sleeve assembly displaces relative to a substantially fixed medicament barrel, in the device 300, the medicament barrel displaces relative to a substantially fixed valve sleeve assembly, as subsequently described in greater detail. Although the valve sleeve assembly is moved to the opposite end of the medicament barrel, the function is still the same with the outer needle creating a sterile tunnel for the inner needle to move through to make the puncture and allow the medicament to flow.

In addition to the above-noted features, the device 300 includes a trolley 324 that is displaceably disposed in the device body, and a device cover or hood 326. Referring to FIG. 20, to load the medicament barrel 306 into the device body 305, a pharmaceutical company, end user, or other entity (for brevity, a user) inserts the medicament barrel 306 into the trolley 324, and then locks the hood 326 onto the device body 305. As subsequently described in greater detail, the design of the device 300 permits medicament barrel loading 306 under conditions that are not aseptic, yet enables a sterile connection.

Referring back to FIGS. 18 and 19, the device 300 also includes a safety pin 316, a needle shield or cover 318, and a needle shield remover 320. In a safety configuration, the safety pin 316 extends from the bottom through the device 300, and up through the top and bottom button portions 30 and 310 to prevent the top button portion 308 from moving (and thereby prevent device activation) until the safety pin 316 is removed.

According to one embodiment, the safety pin 316 and the needle shield 318 are both connected to the needle shield remover, which has a handle portion 322 for gripping. In operation, a user lifts and pulls the handle portion 322 to remove the needle shield 318 and the needle shield 318, thereby uncovering the patient needle, disengaging the safety pin 316 from the top and bottom button portions 308 and 310, and readying the device 300 for activation.

Figure 21:
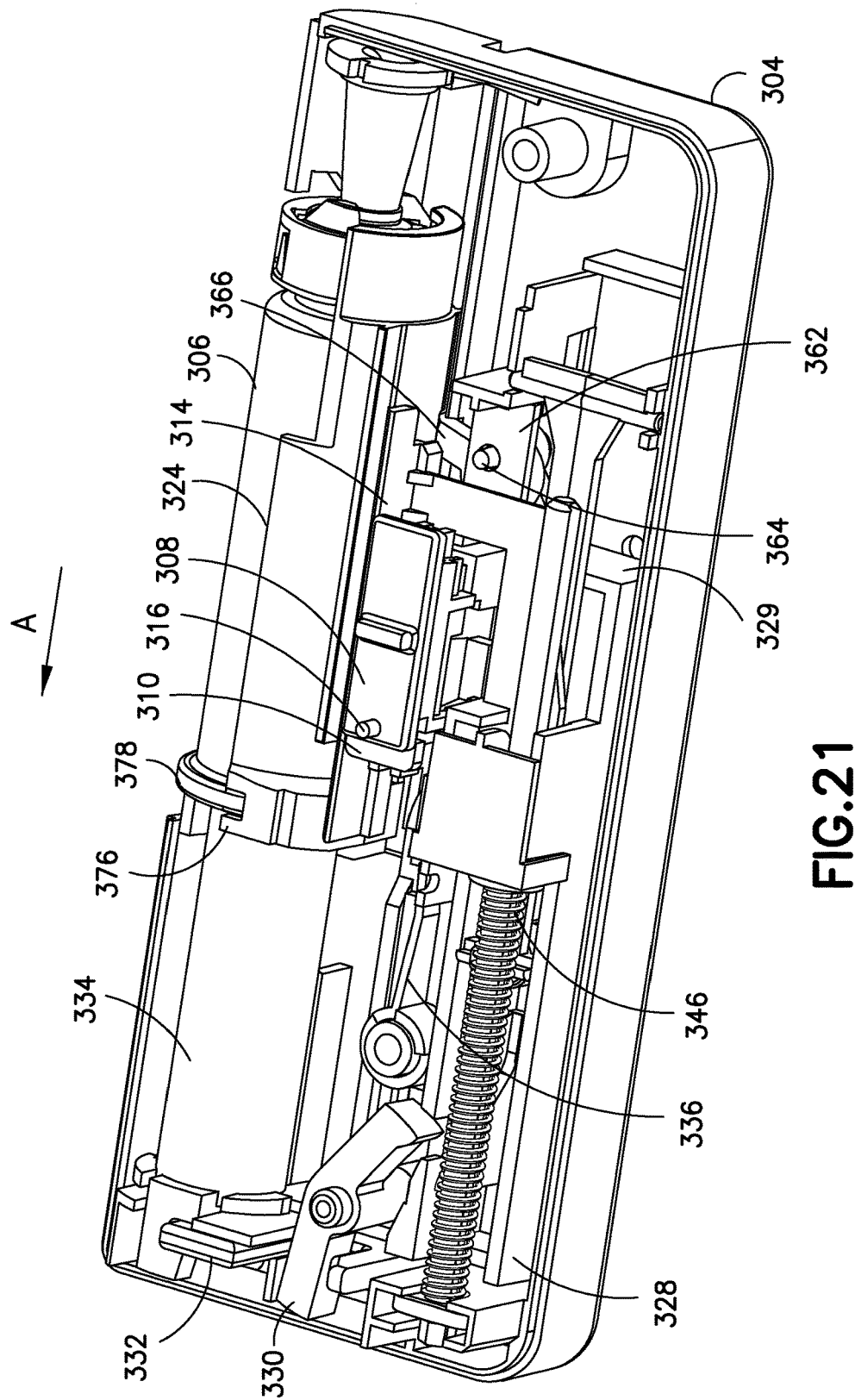
FIG. 21 is a perspective view of the device of FIG. 18 with a top cover and a hood removed for clarity.
Figure 22:
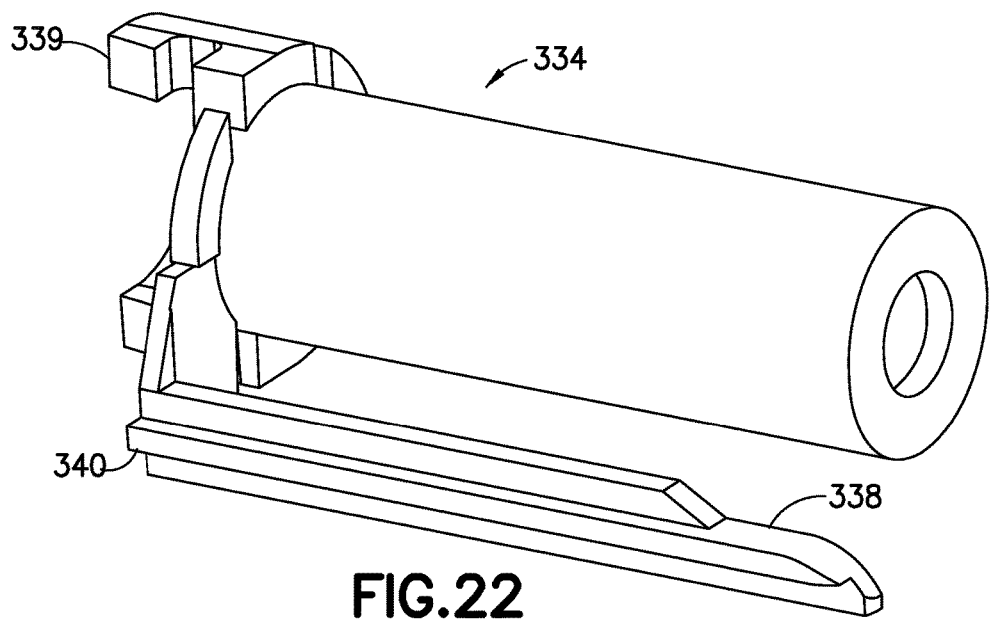
FIG. 22 is a perspective view of a plunger of the device of FIG. 18.
Figure 23:
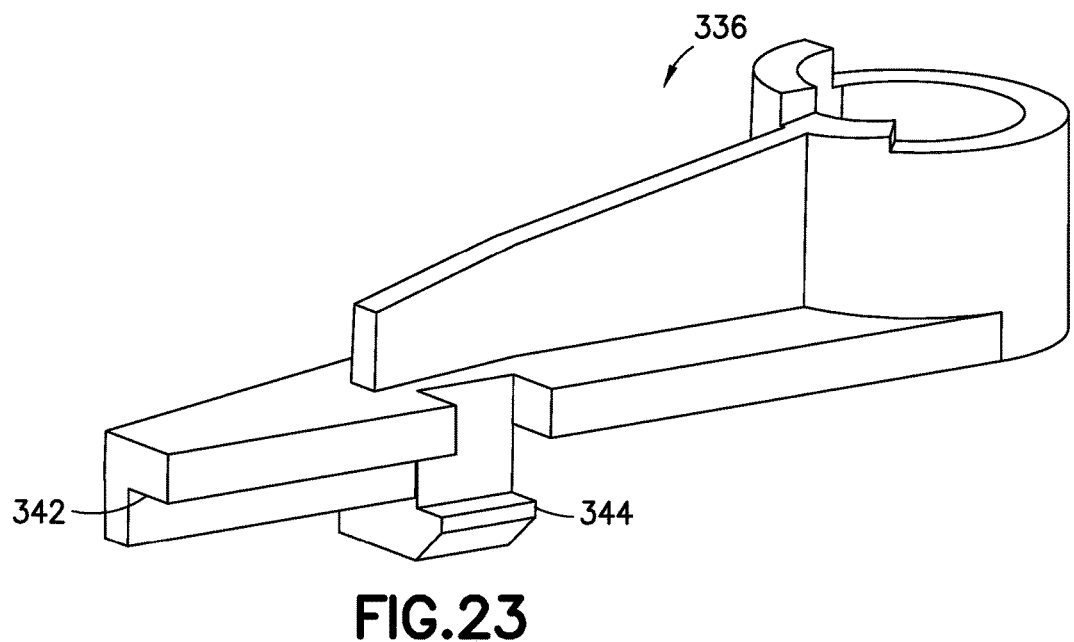
FIG. 23 is a perspective view of a release flipper of the device of FIG. 18.

As shown in FIG. 21, the device 300 includes a needle actuator or slider 328, an activation flipper 330, and a release gate 332 that are similar in shape and function to the corresponding elements in the device 100. The device 300 additionally includes a plunger 334 and a release flipper 336. As shown in FIG. 22, the plunger 334 includes proximal hooks 339 for engaging the release gate 332, and a cantilevered arm 338 with a shelf 340. The release flipper 336, shown in FIG. 23, includes a corresponding shelf 342 and plunger hook 344 that engage the shelf 340 to control the timing of events during operation of the device 300.

Figure 24:
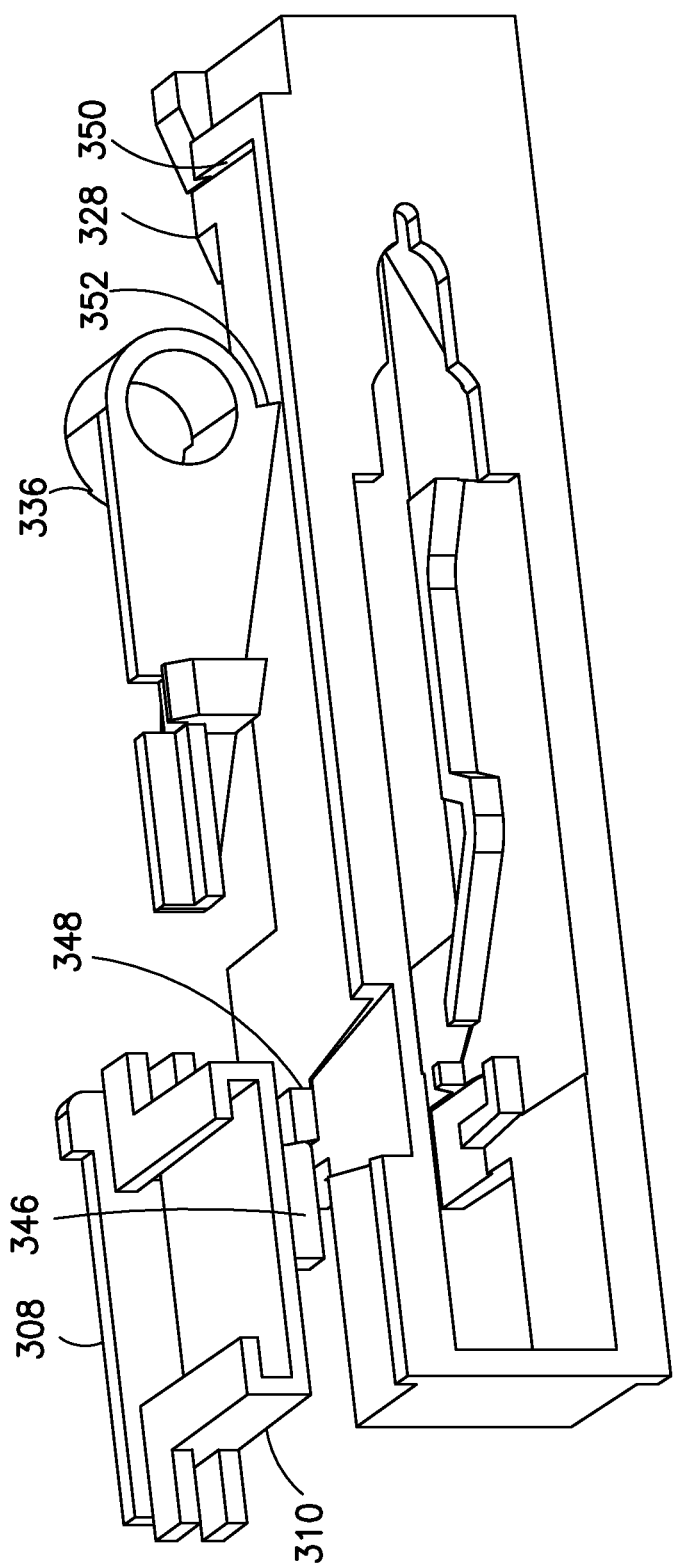
FIG. 24 is a bottom perspective view of top and bottom button portions and a needle actuator of the device of FIG. 18 and the release flipper of FIG. 24.

More specifically, once a user activates the device 300 by sliding the top button portion 308 in a proximal direction (direction A shown in FIG. 21), and then depressing both button portions 308 and 310, a protrusion 346 on the bottom button portion 310 disengages from the a protrusion 348 on the needle actuator or slider 328, permitting the spring 346 to displace the needle actuator 328 distally (opposite to direction A) by a predetermined distance to an intermediate position in which a needle actuator catch 350 engages a needle actuator hook 352 on the release flipper 336 (best shown in FIG. 24). The engagement between the plunger's cantilevered arm 338 and the release flipper's shelf 342 and plunger hook 344 prevents the release flipper from rotating, and thus, maintains the engagement between the hook 352 and the catch 350, thereby maintaining the needle actuator's position.

Additionally, as the needle actuator 328 displaces to the intermediate position, the distal end 329 of the needle actuator 328 rotates the activation flipper 330 counterclockwise, thereby sliding the release gate 332 out of engagement with the plunger's proximal hooks 339, and permitting the plunger to displace distally under the force of a plunger spring 354 and displace displacing a stopper spacer 356 and a stopper 358.

Figure 25:
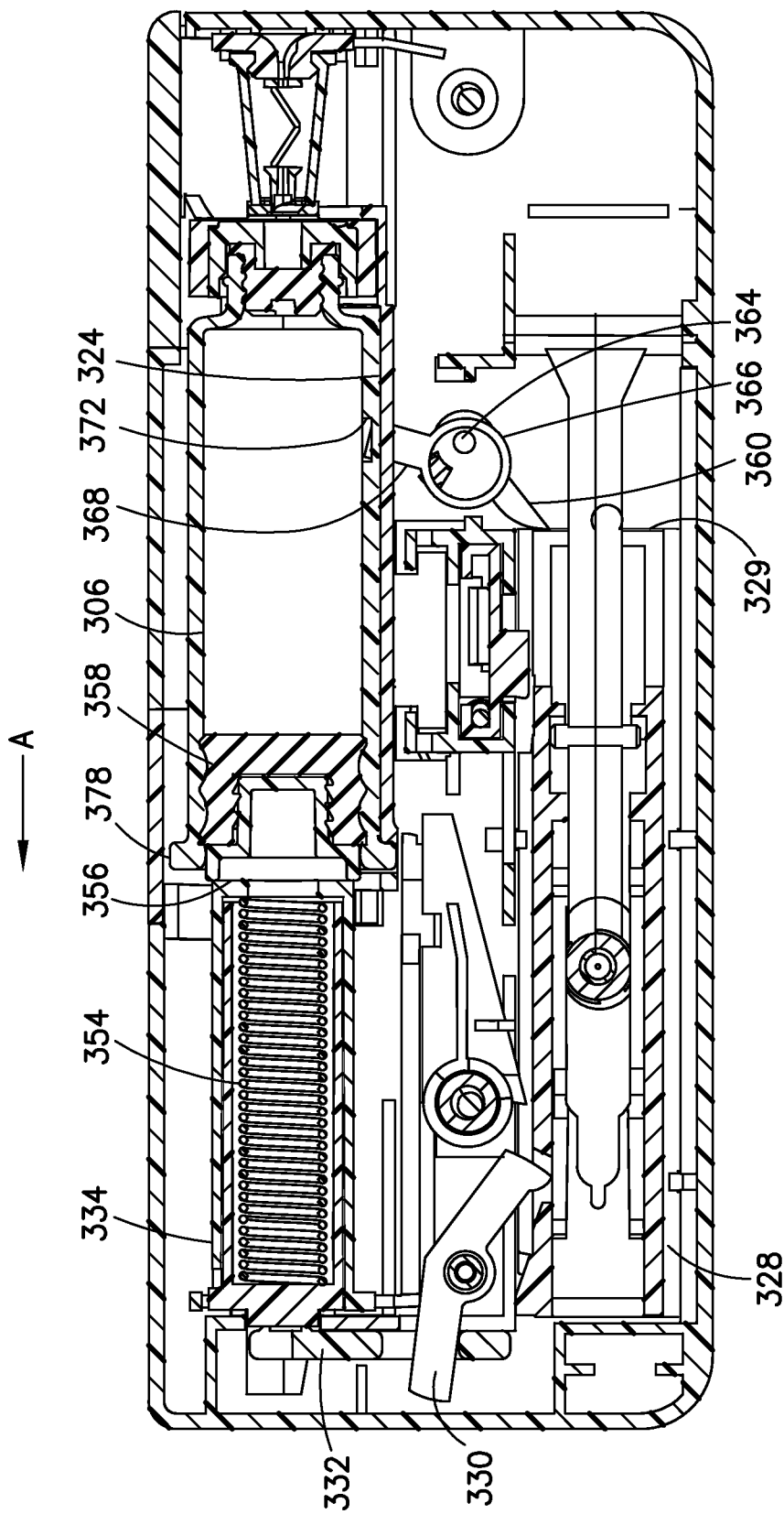
FIG. 25 is a cross-sectional view of the device of FIG. 18 prior to activation.
Figure 26:
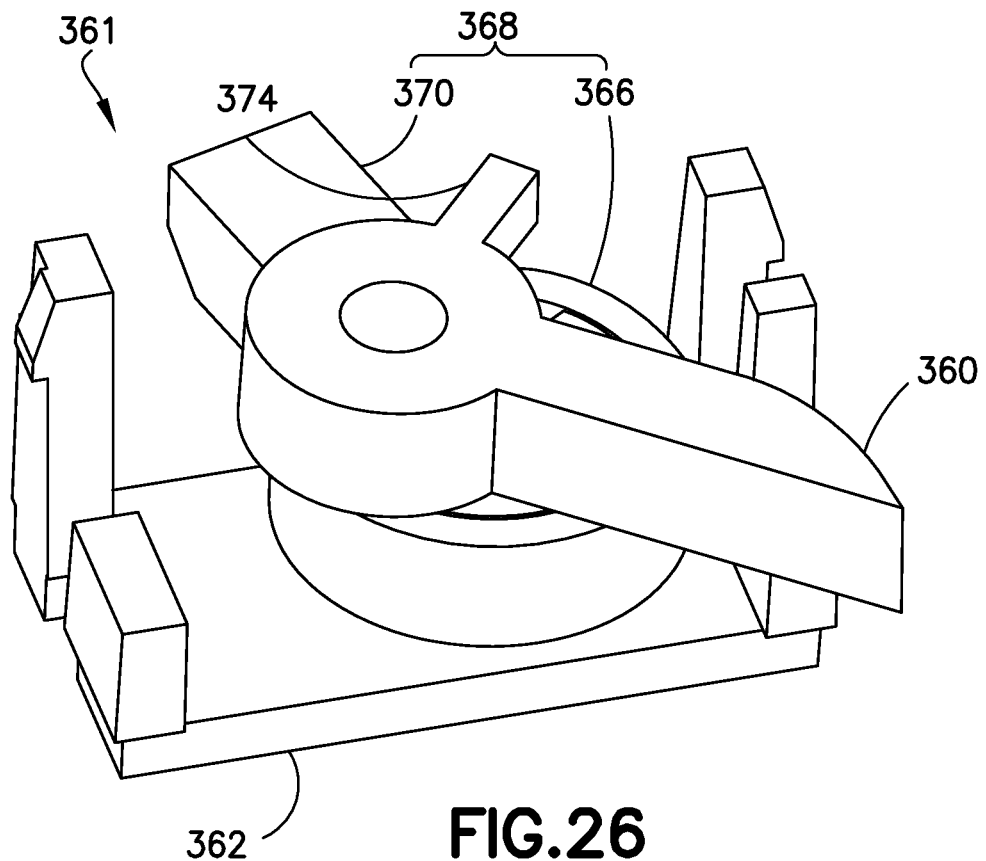
FIG. 26 is a bottom perspective view of a trolley latch assembly of the device of FIG. 18.

Controlling movement of the trolley 324 is important because a premature movement of the medicament barrel 306 could puncture the membranes (394 and 406, subsequently described in greater detail) and create a sterility breach. To control the movement of the trolley 324 and assure that it does not move until the desired time, the trolley 324 is selectively held in position by a trolley latch assembly 361. As shown in FIG. 25, prior to activation, the distal end of the needle actuator 328 is adjacent to a trolley latch 360. According to the embodiment shown in FIG. 25, the needle actuator 328 contacts the trolley latch 360 prior to activation. According to another embodiment, however, prior to activation, the needle actuator 328 and the trolley latch 360 are spaced apart. Although shown in FIGS. 21 and 26, a trolley latch snap bridge 362 that rotatably supports a top post 364 of the trolley latch 360 is omitted from FIG. 25 for clarity. The top post 364 extends through an annular cam portion 366 of a trolley stop 368, as shown in the bottom perspective view of the trolley latch assembly 361 in FIG. 26.

In addition to the cam portion 366, the trolley stop 368 includes a stop portion 370, which engages a recess or opening 372 in the trolley 324 prior to device activation to prevent the trolley from moving. The trolley latch 360 also includes a bottom protrusion 374 that prevents the trolley latch from freely rotating an amount sufficient to dislodge the stop portion 370 from the recess 372, and thus serves as a secondary safety to prevent trolley movement prior to activation.

Subsequent to activation, as the needle actuator 328 displaces to the intermediate position under the force of the spring 346, the distal end of the needle actuator 328 contacts and rotates the trolley latch 360 counter-clockwise with a force sufficient to preferably fracture and snap off the bottom protrusion 374 when it contacts a post in the bottom cover 304. As the trolley latch 360 rotates, the top post 364 interacts with the cam portion 366 to disengage the stop portion 370 from the recess 372, thereby permitting the trolley 324 to displace distally under the force of the plunger spring 354.

In greater detail, the trolley 324 has proximal hooks 376 that engage a proximal rim or flange 378 of the medicament barrel 306. Because the medicament barrel 306 is sealed and filled with a substantially incompressible fluid, once the trolley stop 368 disengages from the trolley 324, the force of the plunger spring 354 acting on the stopper 358 (via the plunger 334 and the stopper spacer 356) displaces the trolley 324 distally due to the engagement between the proximal hooks 376 and the proximal rim 378.

Figure 27:
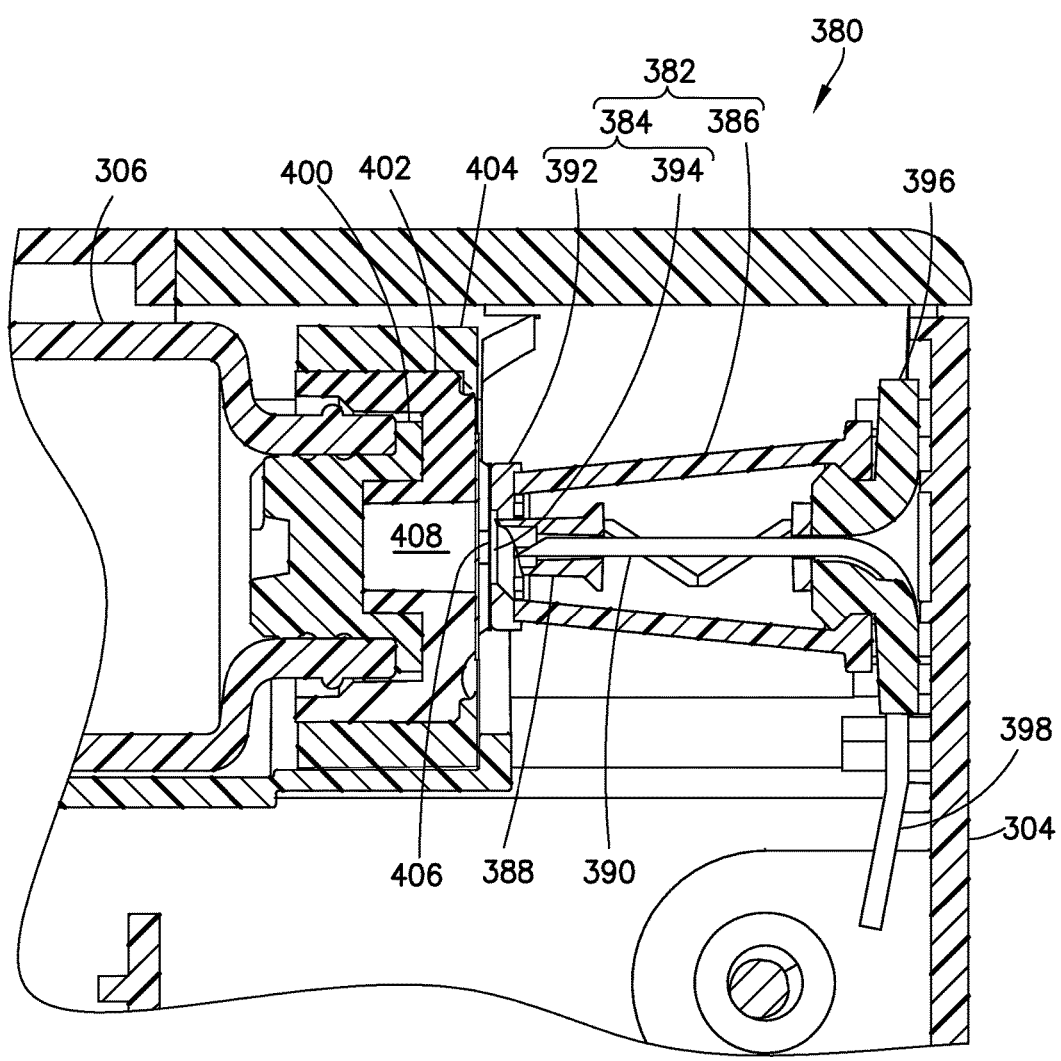
FIG. 27 is a partial cross-sectional view of the device of FIG. 18.

FIG. 27 illustrates a state immediately prior to penetration of sterile barriers. More specifically, as shown in FIG. 27, a valve sleeve assembly 380 includes a two-part flexible sleeve 382 (which includes a barrier portion 384 and a flexible portion 386), a hollow first penetrator or outer needle 388, and a hollow second penetrator or inner needle 390. Preferably, everything inside the flexible sleeve 382 is sterile. The barrier portion 384 includes a cap 382 disposed at the proximal end of the flexible portion 386, and a membrane 394 disposed across an opening at the proximal end of the cap 382. The distal end of the flexible portion 386 is connected to a needle shield holder 396, which is fixedly secured with the bottom cover 304. The inner needle 390 is fixedly secured to the shield holder 396, and is connected with the patient needle via a tube 398.

The medicament barrel 306 has a sealing member or septum 400 disposed at its distal end, and a protective cap 402 and a cap 404 maintain the septum 400 at the distal end of the barrel 306. A barrier or membrane 406 is disposed across an opening at the distal end of the protective cap 402. Together, the septum 400, the protective cap 402, and the membrane 406 form a chamber 408 in fluid communication with the septum. Preferably, at least the surface of the septum 400 exposed in the chamber 408 is sterile, and more preferably, the chamber 408 is sterile.

In the state illustrated in FIG. 27, the membrane 406 and the membrane 394 are disposed adjacent to each other. According to one embodiment, this is the relative position of the valve sleeve assembly 380 and the medicament barrel 306 prior to activation. Preferably, however, the membrane 406 and the membrane 394 are spaced apart prior to activation, and the state illustrated in FIG. 27 occurs subsequent to a predetermined trolley 324 displacement.

Figure 28:
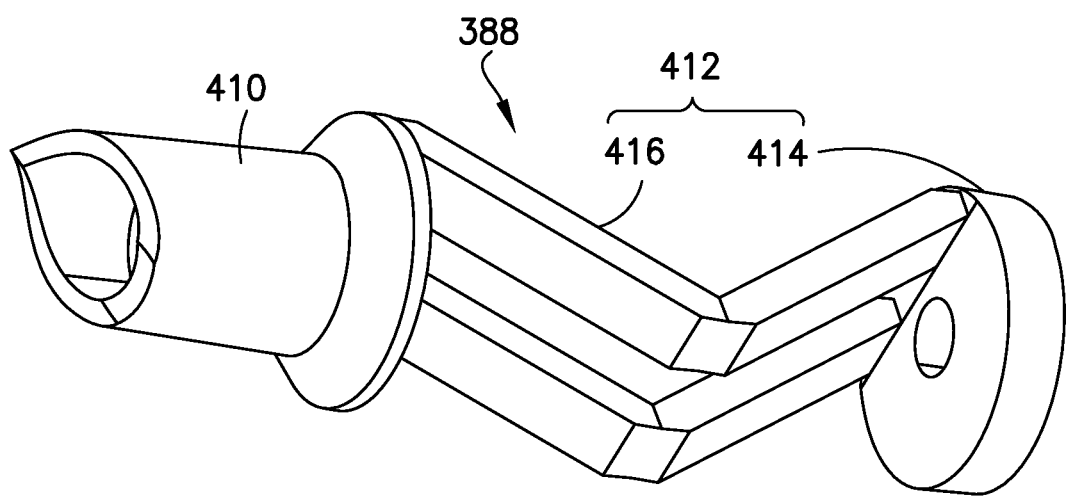
FIG. 28 is a perspective view of a first penetrator of the device of FIG. 18.

Subsequent to the state illustrated in FIG. 27, as the trolley 324 displaces the medicament barrel 306 distally, the flexible portion 386 collapses, and the outer needle 388 pierces both membranes 394 and 406. As shown in FIG. 28, in this embodiment, the first penetrator or outer needle 388 includes a rigid, sharpened penetrating portion 410, and a collapsing portion 412. The collapsing portion includes a base 414 with a hole therethrough for the second or inner penetrator 390, and at least one, but preferably a pair of collapsible legs 416 connecting the base 414 and the penetrating portion 410. Although not shown, according to one embodiment, the penetrating portion includes a guide disposed therein to guide the displacement of the penetrating portion relative to the inner needle 390.

According to one embodiment, the crush force required to bend the legs 416 is selected to be greater than the force required to collapse the flexible portion 386 of the flexible sleeve 382. This relative force profile ensures the timing of events so that the flexible portion 386 collapses prior to the legs 416 bending. In other words, this relative force profile ensures that the penetrating portion 410 pierces the membranes 394 and 406 prior to the legs bending and the penetrating portion 410 displacing relative to the inner needle 390 and exposing the proximal end of the inner needle, thereby maintaining the sterility of the inner needle 390.

Subsequent to the legs 416 bending to displace the penetrating portion 410 relative to the inner needle 390 and expose the proximal end of the inner needle 390, and as the trolley 324 continues to displace the medicament barrel 306 distally, the proximal end of the inner needle 390 passes through the chamber 408 without contacting either of the membranes 394 and 406, and the force from the plunger spring 354 impales the septum 400 on the inner needle 390 so that the proximal end of the inner needle 390 pierces the septum 400. This creates a sterile connection between the medicament in the interior of the medicament barrel 306 and the patient needle, which is fluidly connected with the inner needle 390.

Figure 29:
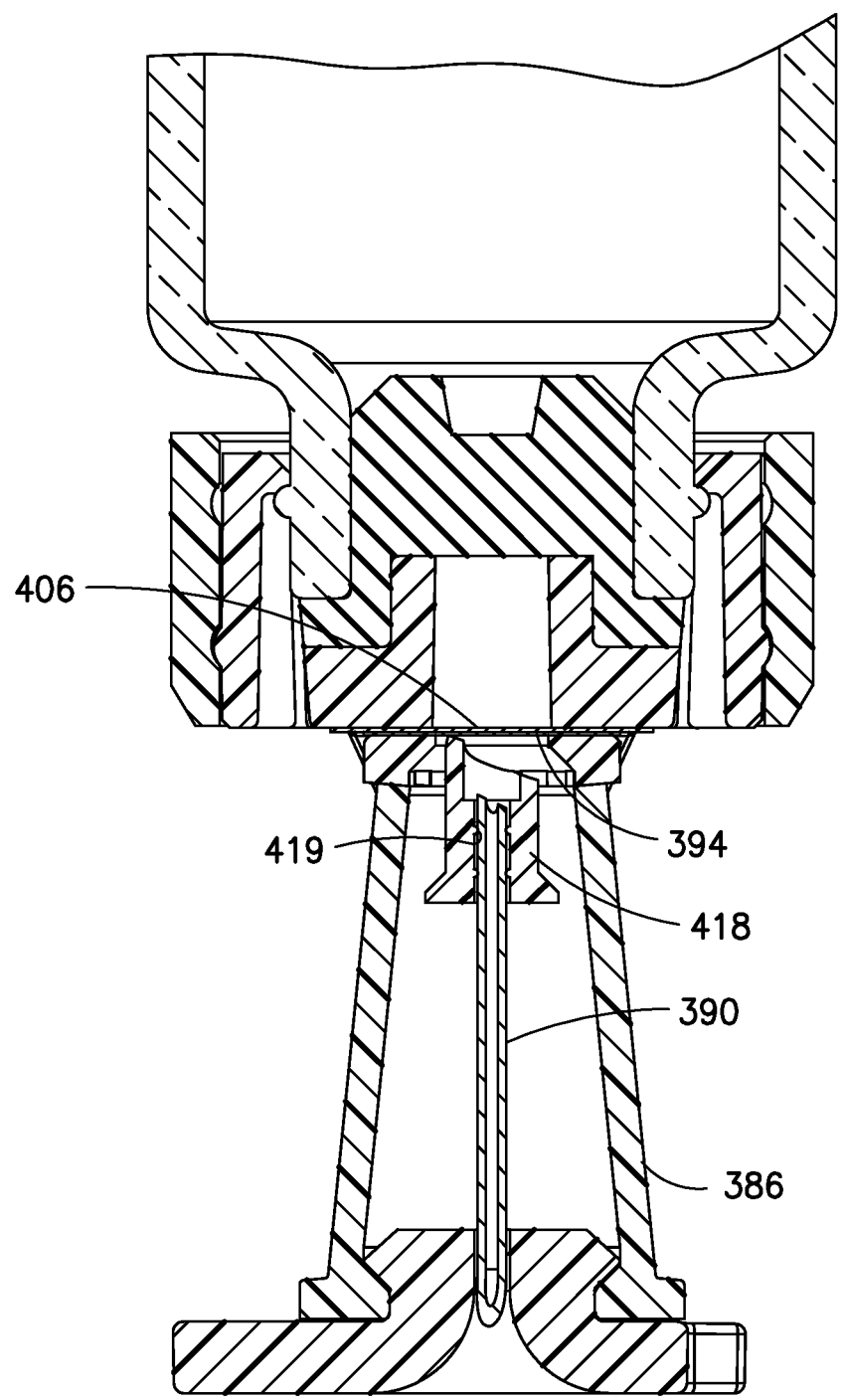
FIG. 29 is a partial cross-sectional view of another double-puncture mechanism in accordance with an embodiment of the present invention.

FIG. 29 is a partial cross-sectional view of another double-puncture mechanism in accordance with an embodiment of the present invention. The embodiment of FIG. 29 is substantially similar to the embodiment of FIG. 27, except for the first penetrator or outer needle 418. The first penetrator 418 includes a rigid, sharpened penetrating portion, but rather than a collapsing portion, instead includes one or more internal contact ribs 419, which can be, for example, insert-molded. The contact ribs 419 provide frictional resistance between the outer needle 418 and the inner needle 390, to ensure that the that the outer needle 418 pierces the membranes 394 and 406 prior to the inner needle 390 displacing relative to the outer needle 418. In other words, the force to collapse the flexible portion 386 is selected to be less than the force to displace the outer needle 418 relative to the inner needle 390.

Referring back to FIGS. 21-25, once the fluid connection is established between the patient needle and the interior of the medicament barrel 306, the plunger displaces further distally under the influence of the plunger spring 354, displacing the stopper spacer 356 and the stopper 358 (best shown in FIG. 25) relative to the medicament barrel 306 and dispensing the medicament. After displacing distally by a predetermined distance (when a predetermined amount of the medicament has been dispensed), the cantilevered arm 338 disengages from the release flipper 336, thereby permitting the release flipper to rotate counter-clockwise as shown in FIGS. 21 and 25 under the influence of the spring 346 pushing on the needle actuator 328. Once the release flipper rotates sufficiently, the hook 352 disengages from the catch 350, freeing the needle actuator 328 to displace distally under the influence of the spring 346, retract the patient needle, and displace the progress indicator 314 relative to the indicator window 312, to indicate that the dosage is complete.

As previously noted the embodiment of the device 300 permits a cartridge (including, for example, the plunger adapter 356, the stopper 358, the medicament barrel 306, the septum 400, the protective cap 402, and the cap 404) to be inserted into the remainder of the device under conditions that are not aseptic, because the sterility of the medicament flow path is ensured by the sealed valve sleeve assembly. Moreover, the cartridge can be sterilized via an ethylene oxide (EtO) sterilization process to avoid yellowing the barrel, and the remainder of the device 300 can be sterilized via gamma irradiation.

Although the previously-described devices and methods for forming a sterile connection are described with respect to infusion and injection devices for human use, other applications can be realized, for example, infusion or injection devices for animals, devices for re-hydrating lyophilized medicament, devices for mixing fluids, such as fluid medications, and devices for re-hydrating freeze-dried food.

Figure 30:
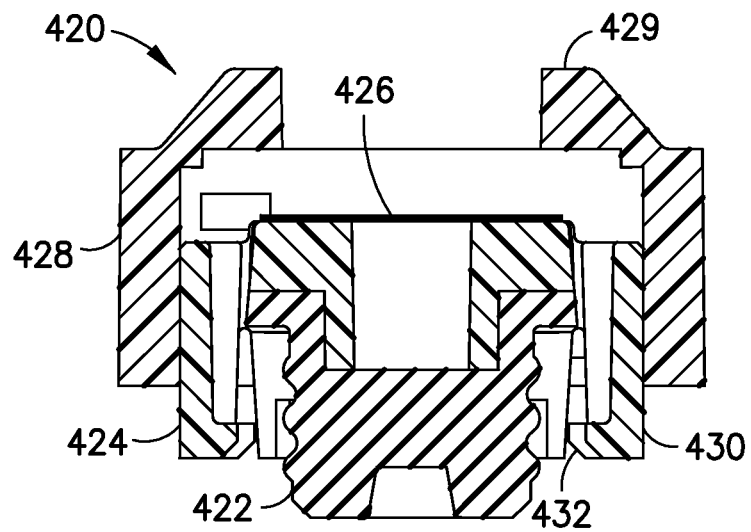
FIGS. 30-32 are partial cross-sectional views illustrating a sealing assembly and a process of employing the sealing assembly to seal an end of a medicament container of the device of FIG. 18.
Figure 31:
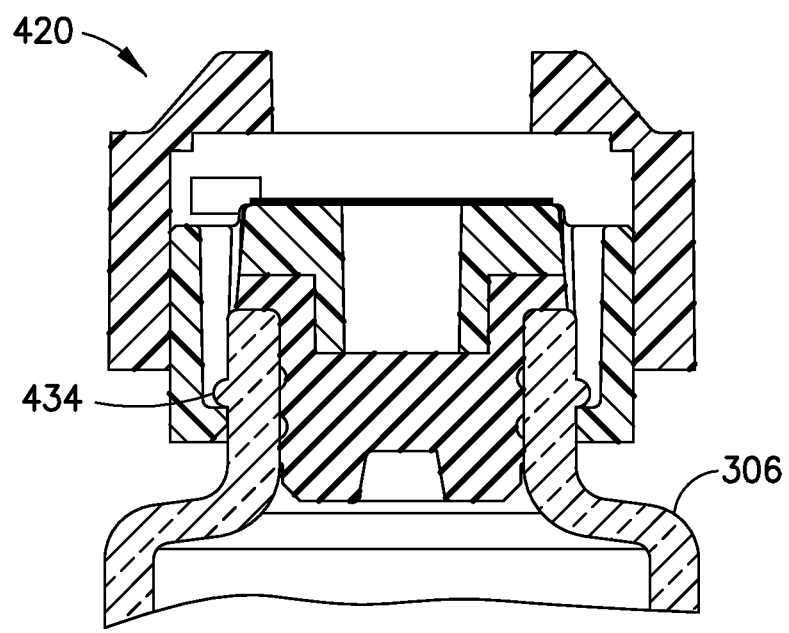
Figure 32:
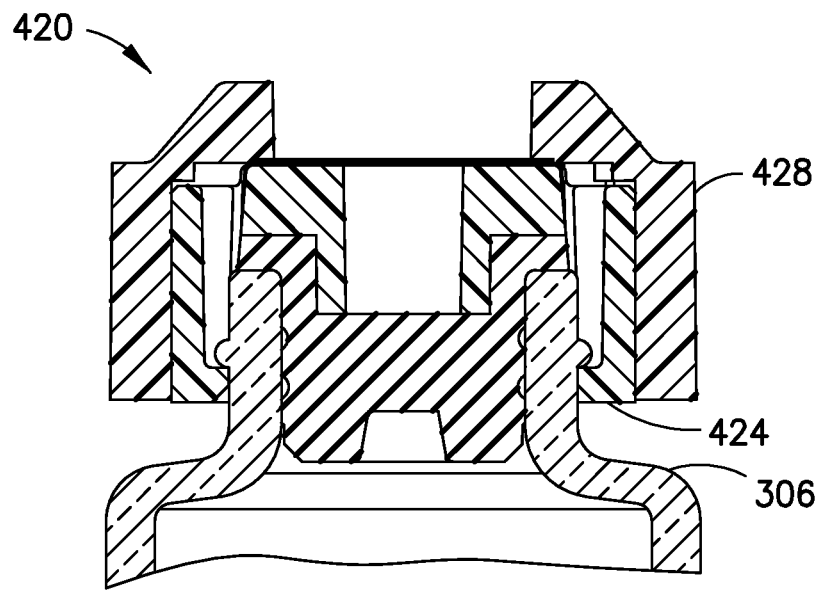

FIGS. 30-32 are partial cross-sectional views illustrating a sealing assembly 420 and a process of employing the sealing assembly 420 to seal an end of the medicament container or medicament barrel 306. The sealing assembly 420 includes a septum 422, a protective cap 424, a sealing membrane 426, and an outer cap 428, as shown in FIG. 30. The cap 428 includes guide features 429 that aid in positioning the end of the flexible sleeve assembly 380 to be adjacent to the membrane 426.

Initially, the manufacturer applies the membrane 426 to cover an opening in the protective cap 424, and inserts the protective cap 424 into a recess in the septum 422 to form an intermediate assembly. At this point, the chamber formed by the septum 422, the protective cap 424, and the membrane 426 is closed, but not yet sterile. The septum 422, the protective cap 424, and the membrane 426 can be sterilized, using, for example, a gamma irradiation technique. Then, the manufacturer places the cap 428 onto an end of the protective cap 424 to form the sealing assembly 420.

As shown in FIG. 31, in a clean room, the manufacturer then inserts the sealing assembly 420 onto an end of a medicament barrel 306 so that the septum 422 seats inside a tip at the end of the barrel 306 and the protective cap 424 secures the subassembly around an outside of the barrel tip. According to one embodiment, one or more protective cap cantilevered arms 430, each having a hook 432, slide around an exterior of the barrel tip until the hook 432 bypasses an annular catch 434 on the barrel 306. Subsequently, as shown in FIG. 32, the manufacturer slides the outer cap 428 down around the protective cap 424, which prevents the hooks 432 from disengaging from the annular barrel catch 434, and thereby secures the sealing assembly 420 to the end of the barrel 306. According to one embodiment, the outer cap 428 compresses the protective cap 444. As a sterilization alternative, the combination of the sealing assembly 420 and the barrel 306 can be sterilized together using, for example, via an EtO sterilization process.

Figure 33:
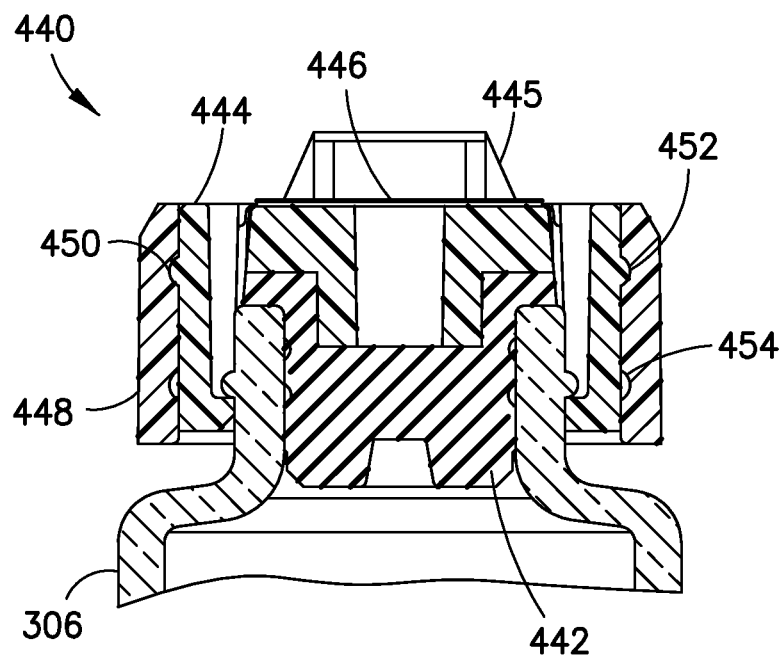
FIG. 33 is a partial cross-sectional view of another sealing assembly in accordance with an embodiment of the present invention.

FIG. 33 illustrates another embodiment of a sealing assembly 440 including a septum 442, a protective cap 444, a sealing membrane 446, and an outer cap 448. The sealing assembly 440 is substantially similar to the sealing assembly 420, except that the guide features are disposed on the protective cap 444, not on the outer cap 448. In addition, the protective cap 444 includes an annular feature 450 on an exterior surface, and the cap 448 includes a pair of annular recesses 452 and 454 on an interior surface. During assembly, the annular feature 450 engages the first recess 454 to maintain the relative positions of the intermediate assembly and the cap 448 as the sealing assembly 440 is inserted onto the end of the barrel 306.

Subsequent to securing the sealing assembly into and around the barrel tip, the manufacturer slides the outer cap 448 relative to the protective cap 444 so that the annular feature 450 engages the second recess 452 (as shown in FIG. 33) to secure the sealing assembly 420 to the barrel tip. According to another embodiment (not shown), the protective cap 444 has an additional annular feature 450 so that when the manufacturer slides the outer cap 448 relative to the protective cap 444 to secure the sealing assembly 420 to the barrel tip, the annular features 450 respectively engage both of the recesses 452 and 454.

Although only a few embodiments of the present invention have been shown and described, the present invention is not limited to the described embodiments. Instead, it will be appreciated by those skilled in the art that changes may be made to these embodiments without departing from the principles and spirit of the invention. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

The invention claimed is:

1. An apparatus for making a sterile connection, comprising:
   a container;
   a sealing member sealing a first end of the container;
   a barrier sealing a chamber in fluid communication with the sealing member; and
   a valve sleeve assembly, comprising:
      a flexible sleeve having a barrier portion at an end of the flexible sleeve, an interior of the flexible sleeve being sterile;
      a hollow first penetrator adapted to displace relative to the flexible sleeve; and
      a hollow second penetrator at least partially disposed within the first penetrator and adapted to displace relative to the first penetrator and the flexible sleeve;
   wherein in an initial state, the flexible sleeve encloses the first penetrator and a penetrating end of the second penetrator;
   wherein one of the container and the valve sleeve assembly is adapted to displace relative to the remaining one of the container and the valve sleeve assembly;
   wherein the flexible sleeve is adapted to collapse, thereby displacing the outer first penetrator relative to the flexible sleeve to pierce the barrier portion and the barrier; and
   wherein upon further relative displacement between the container and the valve sleeve assembly, subsequent to the piercing of the barrier portion and the barrier, the second penetrator is adapted to displace relative to the first penetrator to pierce the sealing member to create a sterile connection with the interior of the container.

2. The apparatus according to claim 1, further comprising a spacing member interposed between the sealing member and the barrier, and at least partially defining the chamber.

3. The apparatus according to claim 1, wherein a piercing end of the second penetrator that pierces the sealing member does not contact the first penetrator.

4. The apparatus according to claim 1, wherein the first penetrator further comprises:
   a penetrating portion; and
   a collapsing portion connected to the penetrating portion.

5. The apparatus according to claim 4, wherein the collapsing portion comprises an elastomeric material.

6. The apparatus according to claim 4, wherein the collapsing portion comprises:
   a base having a hole therethrough for passage of the second penetrator; and
   at least one leg connecting the base and the penetrating portion.

7. A medical device in which the apparatus according to claim 1 is disposed, wherein the medical device is adapted for delivering medicament within the container to a patient, the medical device comprising:
   a plunger adapted to induce the relative displacement between the container and the valve sleeve assembly; and
   a patient needle fluidly connected to the second penetrator.

8. The device according to claim 7, further comprising:
   a dose status indicator indicating an operating status of the medical device;
   wherein the plunger comprises a cantilevered arm adapted to control timing of withdrawal of the patient needle back into the medical device and timing of a status change indicated by the dose status indicator.

9. The device according to claim 8, further comprising:
   a needle actuator displaceably disposed within the medical device and adapted to control insertion of the patient needle; and
   a release flipper displaceably disposed within the medical device and adapted to contact the plunger's cantilevered arm and, subsequent to the patient needle's extension outside the medical device, prevent displacement of the needle actuator until a predetermined displacement of the plunger has occurred and the cantilevered arm no longer contacts the release flipper.

10. The device according to claim 9, wherein the dose status indicator is fixedly disposed on the needle actuator.

11. The medical device according to claim 7, further comprising
   a needle actuator displaceably disposed within the medical device and adapted to control insertion of the patient needle;
   a release gate displaceably disposed within the medical device and adapted to selectively engage the plunger and prevent plunger displacement; and
   an activation flipper displaceably disposed within the medical device and adapted to contact the needle actuator and release gate and, upon activation of the medical device and displacement of the needle actuator, induce disengagement of the release gate with the plunger to permit plunger displacement.

12. The medical device according to claim 7, further comprising:
   a needle actuator displaceably disposed within the medical device and adapted to control insertion of the patient needle;
   a trolley displaceably disposed within the medical device and adapted to hold the container and control displacement of the container toward the valve sleeve assembly; and
   a locking mechanism, comprising:
      a stop selectively engaging the trolley; and
      a latch adapted to, upon displacement of the latch by the needle actuator, disengage the stop from the trolley, thereby permitting displacement of the trolley toward the valve sleeve assembly.

13. The medical device according to claim 7, further comprising a stopper displaceably disposed in a second end of the container opposite to the first end to define the interior volume of the container;
   wherein the stopper is connected with the plunger.

14. The medical device according to claim 7, wherein:
   the container is fixedly disposed within the medical device; and
   the flexible sleeve is connected with an end of the plunger and the valve sleeve assembly displaces toward the container as the plunger displaces.

15. The medical device according to claim 14, wherein the sealing member comprises a stopper movably disposed within the container.

16. The medical device according to claim 14, wherein:
   the first penetrator includes a cavity;
   the second penetrator is fixedly disposed with respect to the plunger; and the plunger comprises a protrusion on its distal end that enters into the cavity to advance the second penetrator relative to the first penetrator.

17. The medical device according to claim 1, wherein the barrier portion of the flexible sleeve comprises a membrane disposed across an opening at an end of the flexible sleeve.

18. The medical device according to claim 1, wherein the first penetrator comprises at least one internal rib frictionally engaging the second penetrator.

19. The medical device according to claim 1, further comprising:
 a protective cap having:
  a first portion thereof at least partially surrounding the first end of the container; and
  a second portion thereof inserted into a recess in the sealing member;
  wherein the barrier seals on opening in the second portion; and
 an outer cap at least partially surrounding the protective cap and adapted to prevent the protective cap from disengaging from the container.

20. The medical device according to claim 19, wherein the second portion forms at least a portion of the chamber.

21. The medical device according to claim 19, wherein the first portion includes at least one cantilevered arm with a hook at its free end adapted to engage a catch disposed at the first end of the container.

22. A method for creating a sterile connection with a fluid in a container, the container having a sealing member sealing a first end of the container, and a barrier sealing a chamber in fluid communication with the sealing member, the method comprising:
 providing a valve sleeve assembly, comprising:
  a flexible sleeve having a barrier portion at an end of the flexible sleeve, an interior of the flexible sleeve being sterile;
  a hollow first penetrator disposed within the flexible sleeve; and
  a hollow second penetrator at least partially disposed within the first penetrator;
 piercing the barrier portion and the barrier with the first penetrator;
 displacing the second penetrator relative to the first penetrator and the sealing member to pierce the sealing member and establish the sterile connection with an interior of the container.

23. The method according to claim 22, wherein piercing the barrier portion and the barrier with the first penetrator comprises:
 displacing the container toward the valve sleeve assembly;
 contacting the valve sleeve assembly with the container; and
 collapsing at least a portion of the flexible sleeve to pierce the barrier portion and the barrier with the first penetrator.

* * * * *